US010550172B2

United States Patent
Lucas

(10) Patent No.: US 10,550,172 B2
(45) Date of Patent: Feb. 4, 2020

(54) SERPIN REACTIVE CENTER LOOP PEPTIDES AND METHODS OF USE

(71) Applicant: University of Florida Research Foundation, Incorporated, Gainesville, FL (US)

(72) Inventor: Alexandra Rose Lucas, Gainesville, FL (US)

(73) Assignee: University of Florida Research Foundation, Incorporated, Gainesville, FL (US)

(*) Notice: Subject to any disclaimer, the term of this patent is extended or adjusted under 35 U.S.C. 154(b) by 0 days.

(21) Appl. No.: 15/559,867

(22) PCT Filed: Mar. 18, 2016

(86) PCT No.: PCT/US2016/023234
§ 371 (c)(1),
(2) Date: Sep. 20, 2017

(87) PCT Pub. No.: WO2016/154041
PCT Pub. Date: Sep. 29, 2016

(65) Prior Publication Data
US 2018/0319868 A1    Nov. 8, 2018

Related U.S. Application Data

(60) Provisional application No. 62/136,292, filed on Mar. 20, 2015.

(51) Int. Cl.
| | | |
|---|---|---|
| *A61K 38/07* | (2006.01) | |
| *A61K 38/08* | (2019.01) | |
| *A61K 38/10* | (2006.01) | |
| *A61K 38/55* | (2006.01) | |
| *C07K 5/11* | (2006.01) | |
| *C07K 7/06* | (2006.01) | |
| *C07K 7/08* | (2006.01) | |
| *C07K 14/81* | (2006.01) | |
| *A61P 31/22* | (2006.01) | |
| *A61P 29/00* | (2006.01) | |
| *A61K 9/00* | (2006.01) | |
| *A61K 38/00* | (2006.01) | |

(52) U.S. Cl.
CPC ........ *C07K 14/8121* (2013.01); *A61K 9/0019* (2013.01); *A61K 38/07* (2013.01); *A61K 38/08* (2013.01); *A61K 38/10* (2013.01); *A61K 38/55* (2013.01); *A61P 29/00* (2018.01); *A61P 31/22* (2018.01); *C07K 5/1019* (2013.01); *C07K 7/06* (2013.01); *C07K 7/08* (2013.01); *A61K 38/00* (2013.01)

(58) Field of Classification Search
CPC ........ A61K 38/07; A61K 38/08; A61K 38/10; A61K 38/162; A61K 38/55; C07K 5/1019; C07K 7/06; C07K 7/08; C07K 14/01; C07K 14/8121
See application file for complete search history.

(56) References Cited

U.S. PATENT DOCUMENTS

| | | | |
|---|---|---|---|
| 7,514,405 B2 * | 4/2009 | Lucas | A61K 38/55 514/1.1 |
| 7,745,396 B2 | 6/2010 | Lucas | |
| 2006/0147454 A1 | 7/2006 | Ni et al. | |
| 2012/0270793 A1 * | 10/2012 | Lucas | A61K 38/1709 514/16.4 |
| 2014/0050754 A1 * | 2/2014 | Tong | A61K 39/12 424/186.1 |

FOREIGN PATENT DOCUMENTS

| | | | | |
|---|---|---|---|---|
| WO | WO-9941381 A1 * | 8/1999 | ......... | C07K 14/8121 |
| WO | WO-2013035107 A1 * | 3/2013 | ............... | C07K 7/06 |

OTHER PUBLICATIONS

Salerno et al. Noncovalent Active Site Interactions Enhance the Affinity and Control the Binding Order of Reversible Inhibitors of the cAMP-dependent Protein Kinase. The Journal of Biological Chemistry. Oct. 25, 1990, vol. 265, No. 30, pp. 18079-18082. (Year: 1990).*
Ambadapadi et al. Reactive Center Loop (RCL) Peptides Derived from Serpins Display Independent Coagulation and Immune Modulating Activities. The Journal of Biological Chemistry. Nov. 30, 2015, vol. 291, No. 6, pp. 2874-2887. (Year: 2015).*
Bradford et al. Novel Uperin Peptides from the Dorsal Glands of the Australian Floodplain Toadlet Uperoleia inundata. Australian Journal of Chemistry. 1996, vol. 49, pp. 475-484. (Year: 1996).*
International Search Report and Written Opinion dated Jul. 25, 2016 for Application No. PCT/US2016/023234.
International Preliminary Report on Patentability dated Oct. 5, 2017 for Application No. PCT/US2016/023234.
Chen et al., Myxomavirus-derived serpin prolongs survival and reduces inflammation and hemorrhage in an unrelated lethal viral infection. Antimicrobial Agents and Chemotherapy. Sep. 2013;57(9):pp4114-4127.
Dai et al., Identification of myxomaviral serpin reactive site loop sequences that regulate innate immune responses. J. Biol. Chem. Mar. 2006;281(12):pp. 8041-8050.

* cited by examiner

*Primary Examiner* — Jeffrey E. Russel
(74) *Attorney, Agent, or Firm* — Wolf, Greenfield & Sacks, P.C.

(57) ABSTRACT

Disclosed here are peptides derived from a serpin reactive center loop that have anti-inflammatory, anti-atherogenic and anti-sepsis activity. Compositions containing such serpin-derived peptides are therefore useful in the treatment of transplant vascular disease and also for the treatment of hemorrhagic viral infections as well as lethal viral, fungal or bacterial sepsis in patients.

12 Claims, 13 Drawing Sheets

Specification includes a Sequence Listing.

Serp-1 Peptides
FIG. 4A S-1
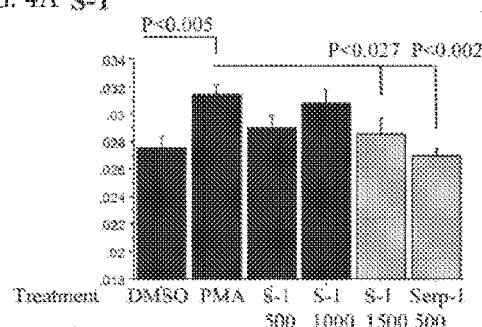
NSP Peptides
FIG. 4B S-2
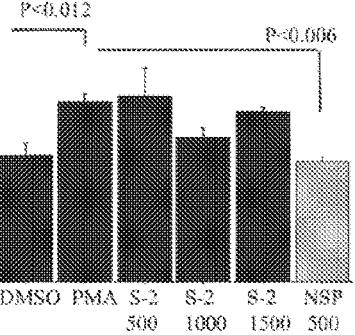
FIG. 4C S-3
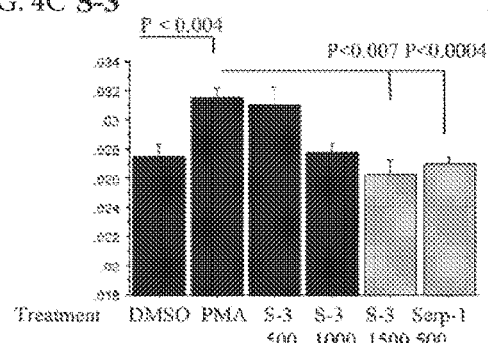
FIG. 4D S-4
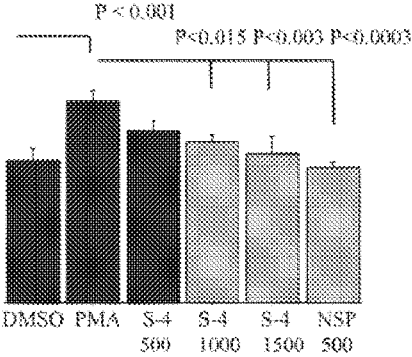
FIG. 4E S-5
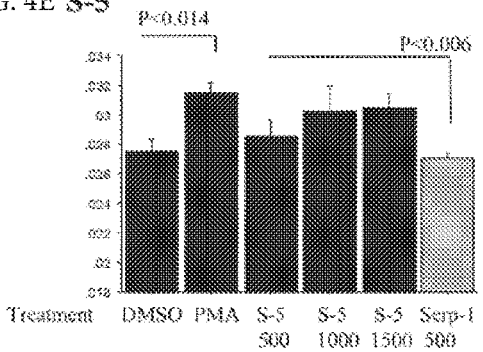
FIG. 4F S-6
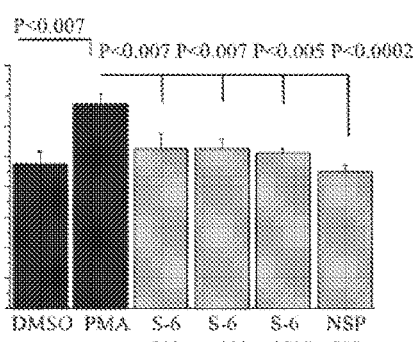
FIG. 4G S-7
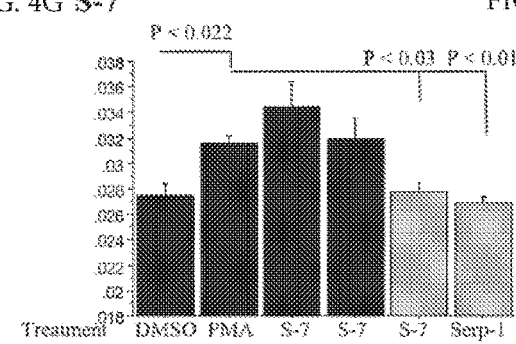
FIG. 4H S-8
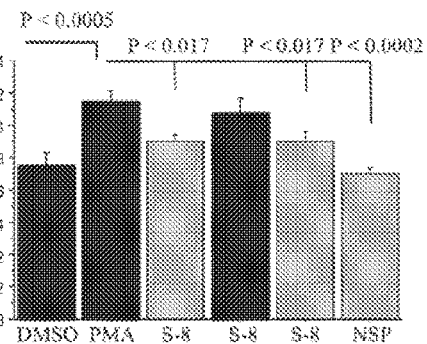

SEQUENCE LISTING

<160> NUMBER OF SEQ ID NOS: 10

<210> SEQ ID NO 1
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 1

Ile Pro Arg Asn Ala Leu
1               5

<210> SEQ ID NO 2
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 2

Ile Ser Arg Met Ala Val
1               5

<210> SEQ ID NO 3
<211> LENGTH: 4
<212> TYPE: PRT

```
<213> ORGANISM: Artificial Sequence
<220> FEATURE:
<223> OTHER INFORMATION: Synthetic polypeptide

<400> SEQUENCE: 3

Arg Asn Ala Leu
1

<210> SEQ ID NO 4
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 4

Ile Ala Ile Ser Arg Met
1               5

<210> SEQ ID NO 5
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 5

Thr Ala Ile Val Ala Asn Lys Pro Phe
1               5

<210> SEQ ID NO 6
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 6

Glu Val Asn Glu Glu Gly Ser Glu Ala Ala Ala Val Ser Gly Met
1               5                   10                  15

<210> SEQ ID NO 7
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 7

Gly Thr Thr Ala Ser Ser Asp Thr Ala Ile Thr Leu Ile Pro Arg
1               5                   10                  15

<210> SEQ ID NO 8
<211> LENGTH: 21
<212> TYPE: PRT
<213> ORGANISM: Artificial Sequence
<220> FEATURE:
<223> OTHER INFORMATION: Synthetic polypeptide

<400> SEQUENCE: 8

Met Ala Val Leu Tyr Pro Gln Val Ile Val Asp His Pro Phe Phe
1               5                   10                  15

Leu Ile Arg Asn Arg
            20

<210> SEQ ID NO 9
```

```
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 9

Ala Ile Thr Leu Ile Pro Arg
1               5

<210> SEQ ID NO 10
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 10

Gly Thr Thr Ala Ser Ser Asp Thr
1               5
```

SERPIN REACTIVE CENTER LOOP PEPTIDES AND METHODS OF USE

RELATED APPLICATIONS

This application is a National Stage Application of PCT/US2016/023234, filed Mar. 18, 2016, entitled "SERPIN REACTIVE CENTER LOOP PEPTIDES AND METHODS OF USE", which claims the benefit under 35 U.S.C. § 119(e) of U.S. Provisional Application Ser. No. 62/136,292, entitled "SERPIN REACTIVE CENTER LOOP PEPTIDES AND METHODS OF USE", filed Mar. 20, 2015, the entire contents of each application which are incorporated herein by reference.

FEDERALLY FUNDED RESEARCH

This invention was made with government support under HL100202 and AI100987 awarded by National Institutes of Health. The government has certain rights in the invention.

FIELD OF THE INVENTION

The present disclosure relates to peptides derived from a serpin reactive center loop and more particularly to serpin-derived peptides that have anti-inflammatory and anti-atherogenic activity and that are useful in, for example, the treatment of transplant vascular disease and also for hemorrhagic viral infections and lethal viral and bacterial sepsis in patients.

BACKGROUND

Severe viral infections and bacterial sepsis are associated with a high mortality rate and limited treatment options. Current therapeutic approaches that target both thrombotic and thrombolytic pathways for the treatment of lethal sepsis result in a 6 to 19% reduction in death. And, although treatment approaches targeting inflammatory pathways have shown some success in clinical trials, a therapeutic approach that can affect innate immune responses through inactivation of serine proteases with minimal coagulopathic and hemorrhagic changes can provide a new treatment strategy for lethal viral infections and sepsis.

SUMMARY

Disclosed herein, are physiologically acceptable compositions comprising polypeptides derived from a reactive site loop of a serine protease inhibitor or a biologically active variant thereof.

Disclosed herein are serpin-derived polypeptides and their amino acid sequences, and methods of treatment of diseases.

2

Figures 1A, 1B:
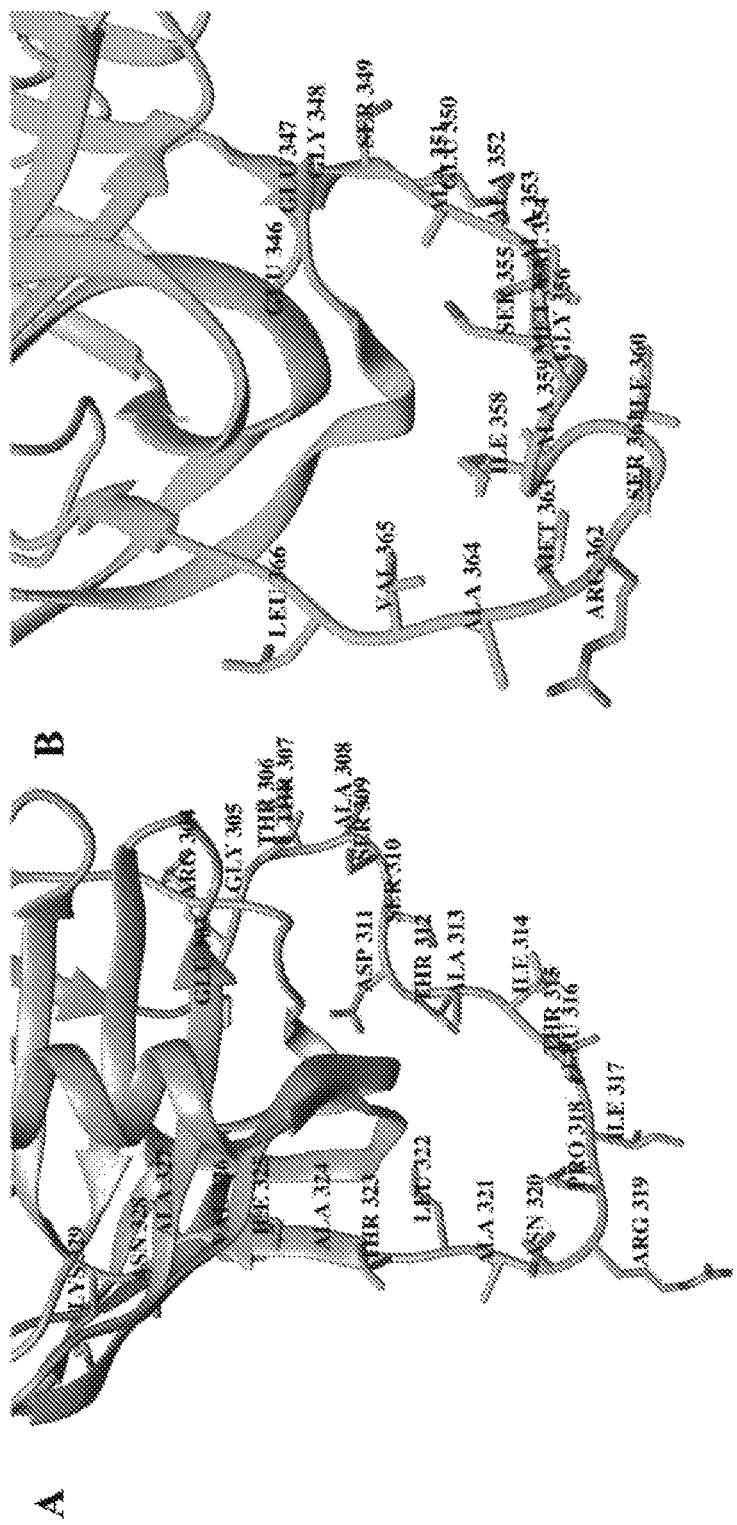
FIGS. 1A-1B show Serp-1 and NSP reactive center loops and serpin peptides. The RCL portions of Serp-1 (FIG. 1A) and NSP (FIG. 1B) are shown along with the peptide sequences and their calculated pI, charge (z) and hydrophobicity (hP) values. RCL portions shown are from a homology model of Serp-1 (sequence UniProtKB/Swiss-Prot: P12393.2) generated by SWISS-MODEL (template, PDB ID: 4DTE) and crystal structure of NSP (PDB ID: 3F5N).

SEQ ID NOs: 1, 3, 5 and 7 are shown top to bottom in FIG. 1A. SEQ ID NOs: 2, 4, 6 and 8 are shown top to bottom in FIG. 1B.

Figure 2:
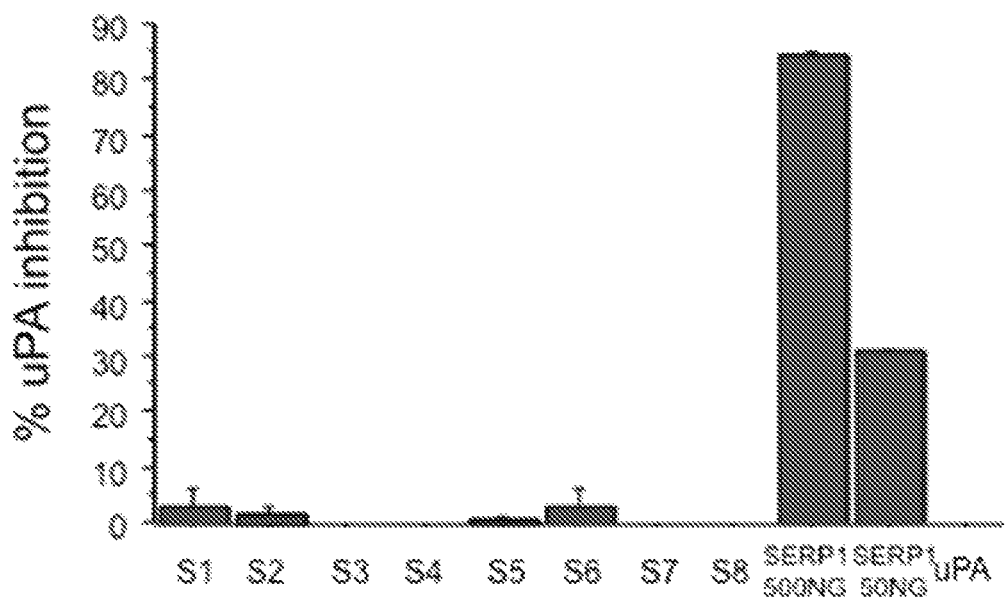

FIG. 2 is a graph depicting the analysis of serpin and serpin-derived peptide inhibition of uPA by chromogenic enzyme activity assay. The results show that Serp-1 inhibition of urokinase-type plasminogen activator (uPA) is dose dependent with greater inhibition at the higher concentration (500 ng). None of the peptides tested had inhibitory activity for uPA.

Figures 3A, 3B, 3C, 3D, 3E, 3F:
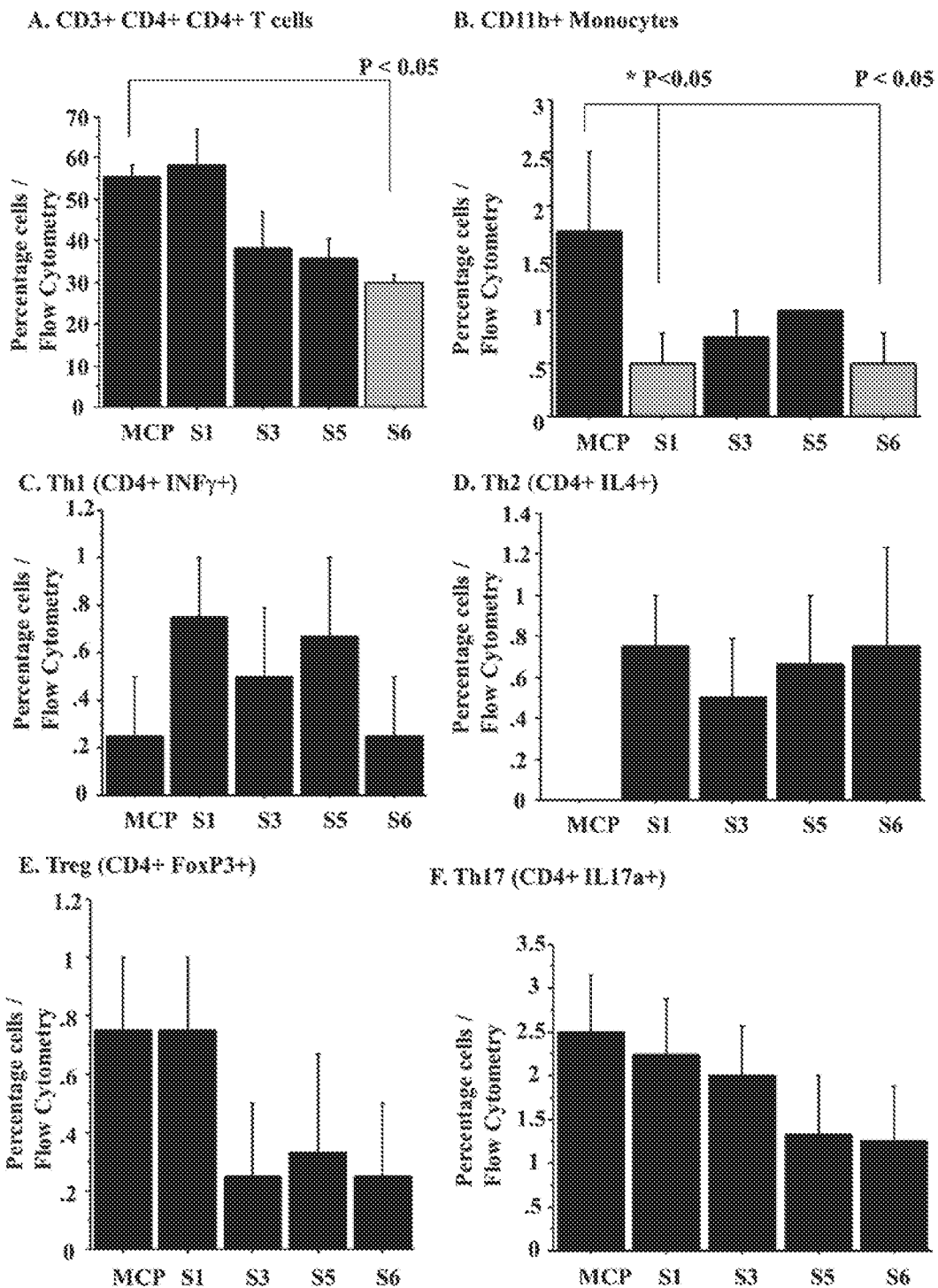

FIGS. 3A-3F provide a graphical illustration showing that serpin-derived peptides modify splenocyte responses after intraperitoneal MCP-1 chemokine injection. Treatment with S-6 peptide significantly reduced splenocyte CD3+ CD4+ T cell isolates at 18 hours (FIG. 3A) while S-1 and S-6 reduced CD11b+mononuclear splenocyte cell isolates (FIG. 3B). Th1 (FIG. 3C), Th2 (FIG. 3D), T reg (FIG. 3E) and Th17 (FIG. 3F) were not significantly altered by peptide treatment, although non-significant trends were detected (n=4-6 mice).

FIGS. 4A-4H show graphs demonstrating that serpin-derived peptides modify cell activation as measured by membrane fluidity in vitro. Serp-1 peptides S-1 (FIG. 4A), S-3 (FIG. 4C) and S-7 (FIG. 4G) and NSP peptides S-4 (FIG. 4D), S-6 (FIG. 4F) and S-8 (FIG. 4H) significantly reduced membrane fluidity in PMA activated THP-1 monocytes. Serp-1 peptide S-5 (FIG. 4E) and NSP peptide S-2 (FIG. 4B) did not reduce membrane fluidity in PMA activated THP-1 monocytes. Serp-1 and NSP consistently reduced membrane fluidity significantly.

FIGS. 5A-5F are graphs showing that serpin-derived peptides display differential effects on gene expression in signaling pathways in human T cells and monocyte/macrophage cell lines. The activation or repression of signaling genes by Serp-1, S-1 and S-3 treatments in Jurkat T cells (FIG. 5A and FIG. 5B) and THP-1 (FIG. 5C-F) monocyte cells were compared to saline treatment. In Jurkat T cells TCF7 gene (FIG. 5A) was repressed by Serp-1 and S-1 but not by S-5, and BCL2 gene (FIG. 5B) was repressed by S-5 treatment whereas S-1 and Serp-1 did not alter gene expression. In THP-1 monocytes CD162 (FIG. 5C), GYS (FIG. 5D) and CDKN4 (FIG. 5E) gene expression was significantly increased by both Serp-1 and S-1 but not by S-5. BRCA1 gene (FIG. 5F) expression was significantly increased by Serp-1 and S-1 treatment and repressed by S-5 when compared to saline treatment.

Figure 6:
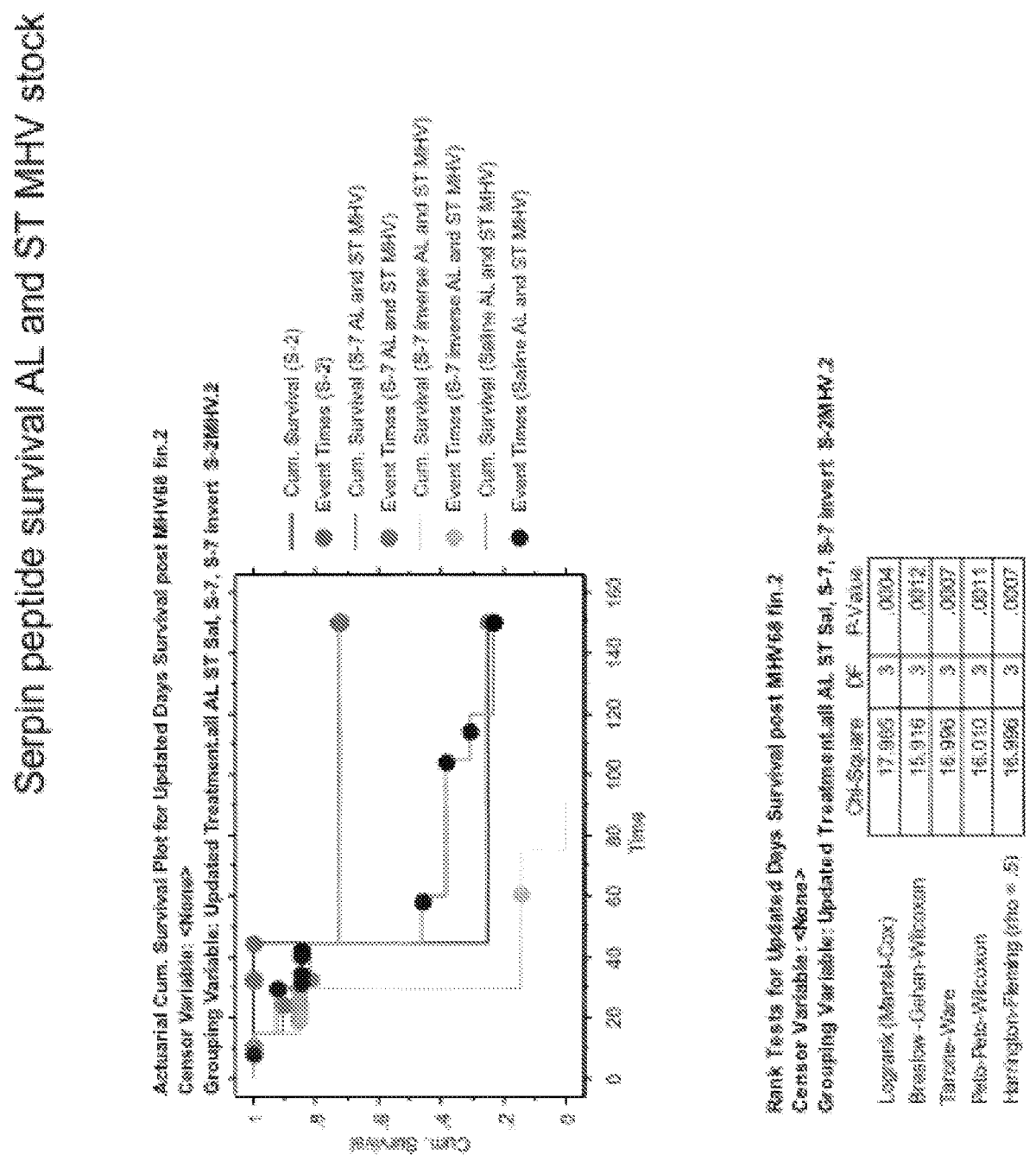

FIG. 6 is a survival curve showing that serpin-derived peptide S-7 improves survival in lethal MHV68-infected interferon gamma receptor deficient mice (IFNgR KO) compared to saline-treated control infected mice. The serpin-derived peptides S-2 and S-7, an inverse sequence, were inactive and did not improve survival.

Figure 7:
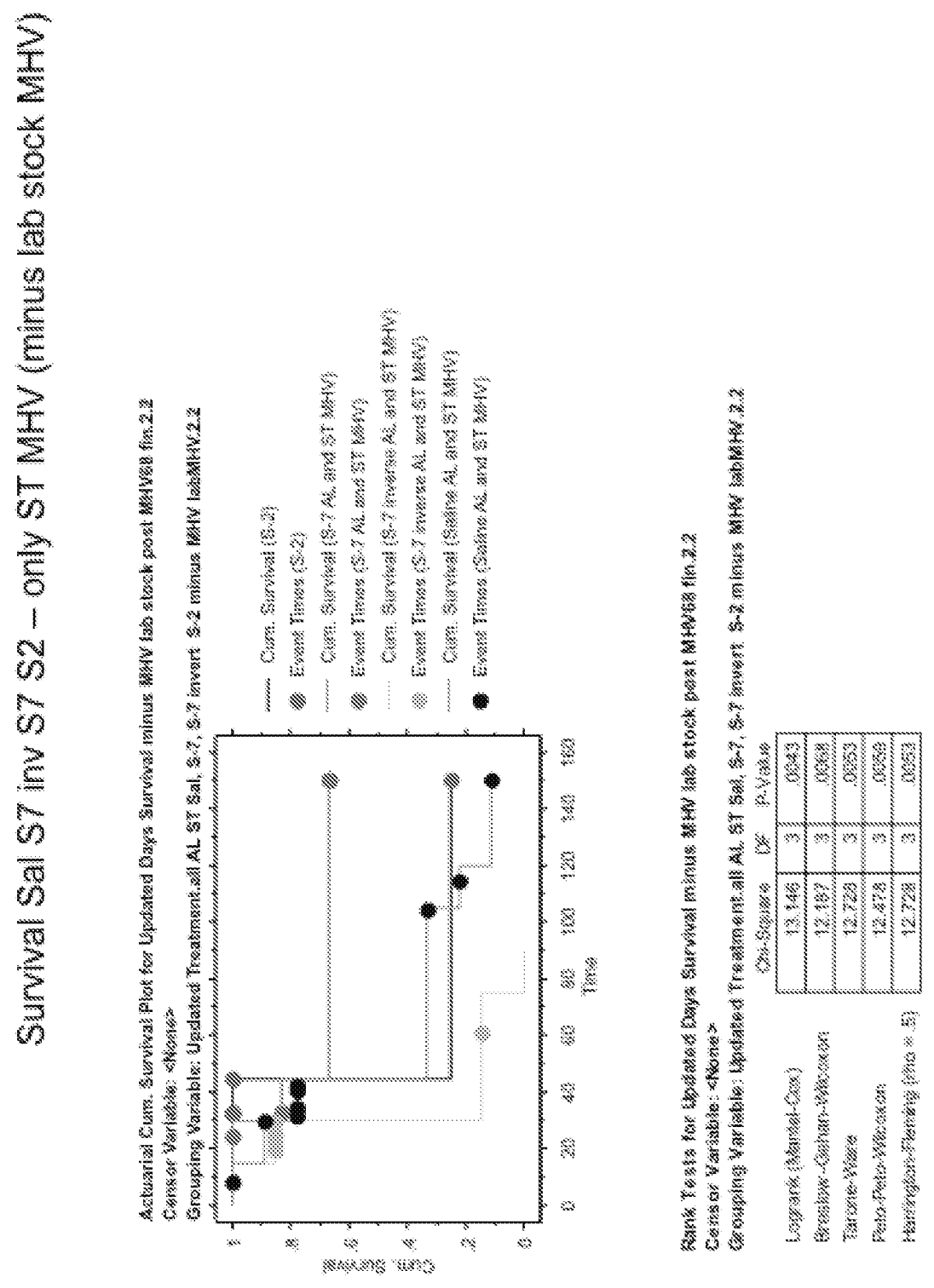

FIG. 7 is a survival curve showing that serpin-derived peptide S-7 improves survival in lethal MHV68-infected interferon gamma receptor deficient mice (IFNgR KO) compared to saline-treated control infected mice. The serpin-derived peptides S-2 and an inverse sequence peptide of S-7 were inactive and did not improve survival.

Figures 8A, 8B, 8C, 8D:
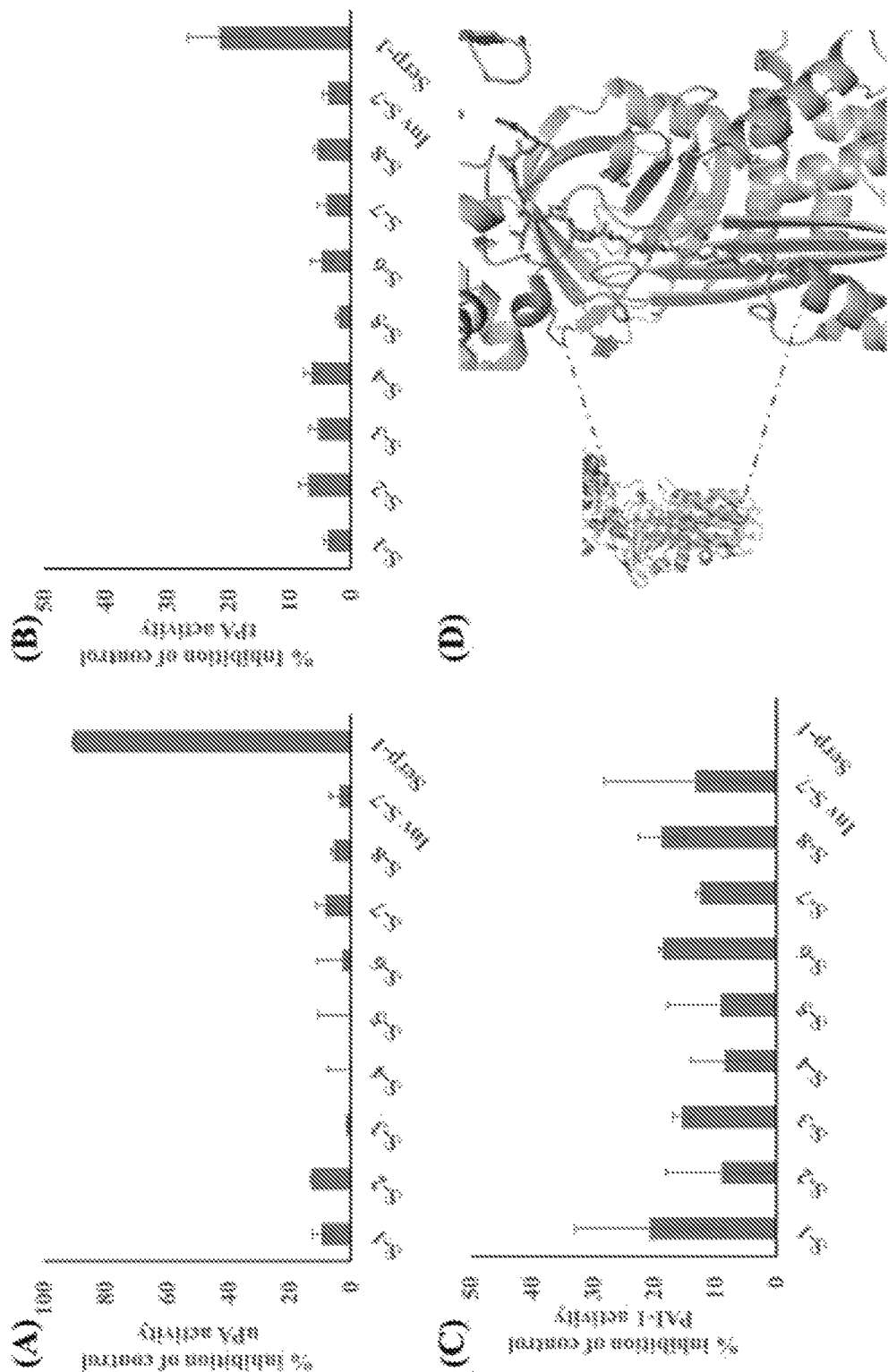

FIGS. 8A-8D show the results of the analysis of serpin and serpin-derived peptide inhibition of uPA, tPA and PAI-1. FIG. 8A shows the inhibition of uPA activity; FIG. 8B shows the inhibition of tPA activity; and FIG. 8C shows the inhibition of PAI-1 activity. FIG. 8D shows the molecular model of S-7 docked in the A-beta sheet of PAI-1.

Figures 9A, 9B, 9C, 9D, 9E, 9F:
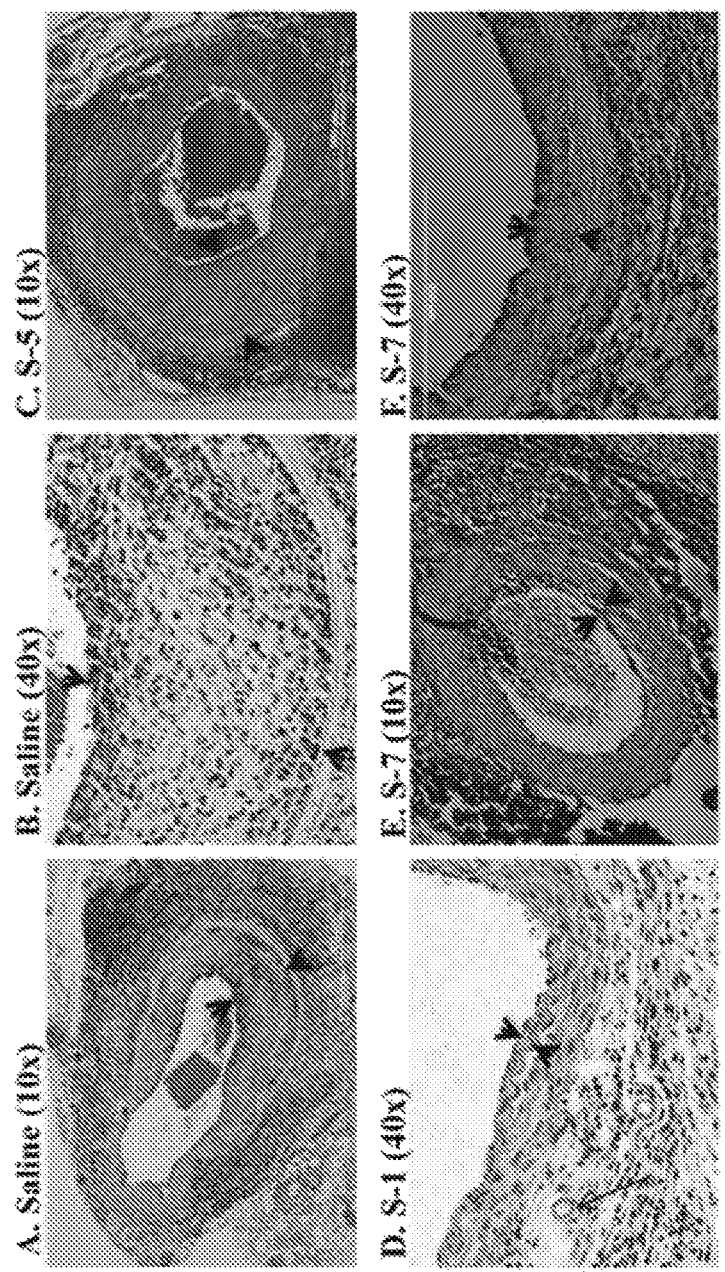
Figures 9G, 9H:
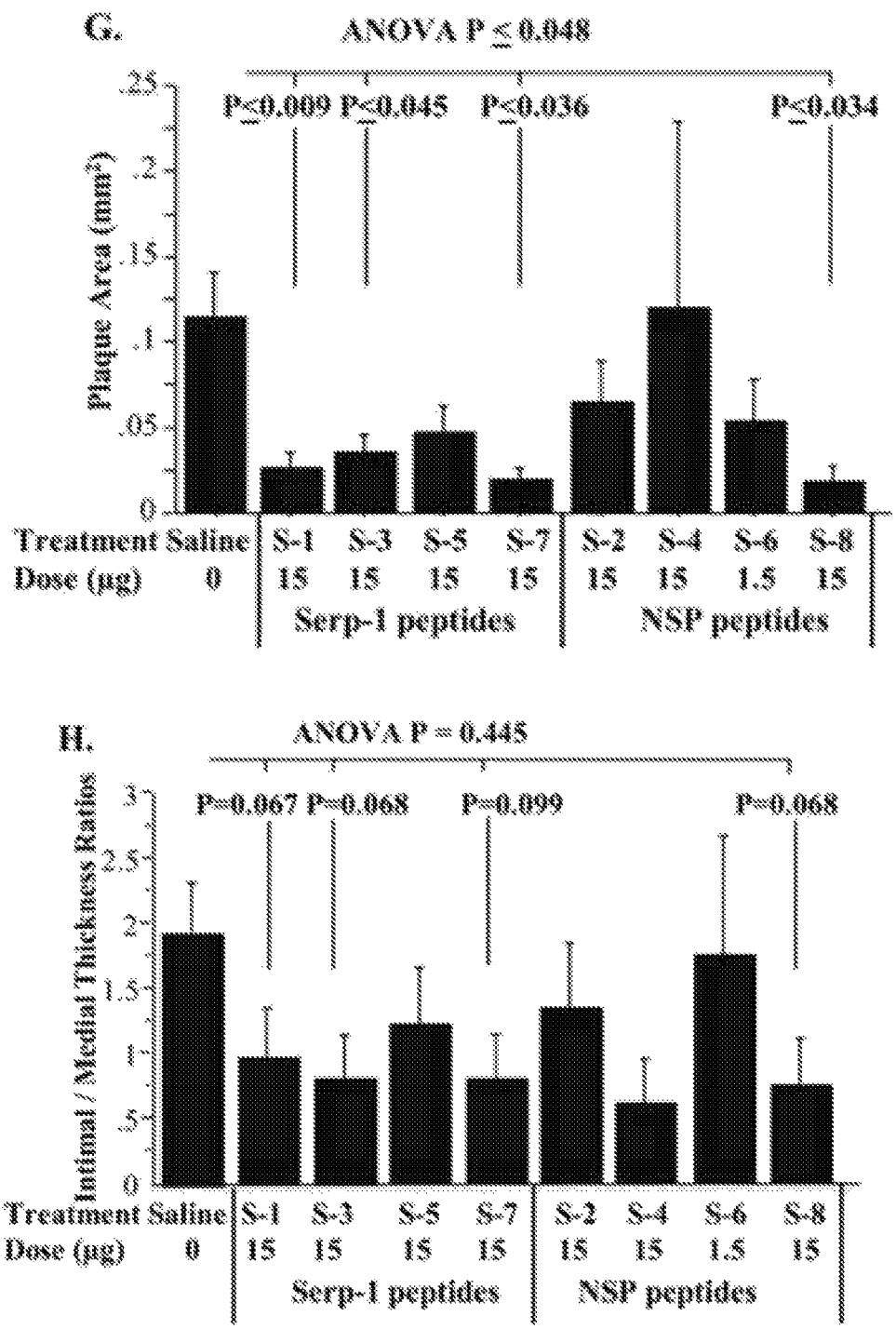

FIGS. 9A-9H show the effects of serpin peptide infusions on plaque growth. Saline (FIG. 9A 10×; FIG. 9B 40×) and S-5 (FIG. 9C, 10×) treated animals display larger plaque areas. S-1 significantly reduced plaque area (FIG. 9D, 40×), as did S-7 (FIG. 9E 10×; FIG. 9F 40×). The intimal hyperplasia is indicated by arrowheads. Long arrow in FIG. 9D shows the suture at the site of transplant. FIG. 9G is a bar graph that demonstrates significant reductions in plaque area by S-1, S-3, S-7 and S-8 peptides. FIG. 9H shows intimal to medial thickness ratios for S-1, S-3, S-7 and S-8; demonstrating a trend towards reduction compared to saline controls. ($P \leq 0.05$ considered significant).

Figures 10A, 10B, 10C:
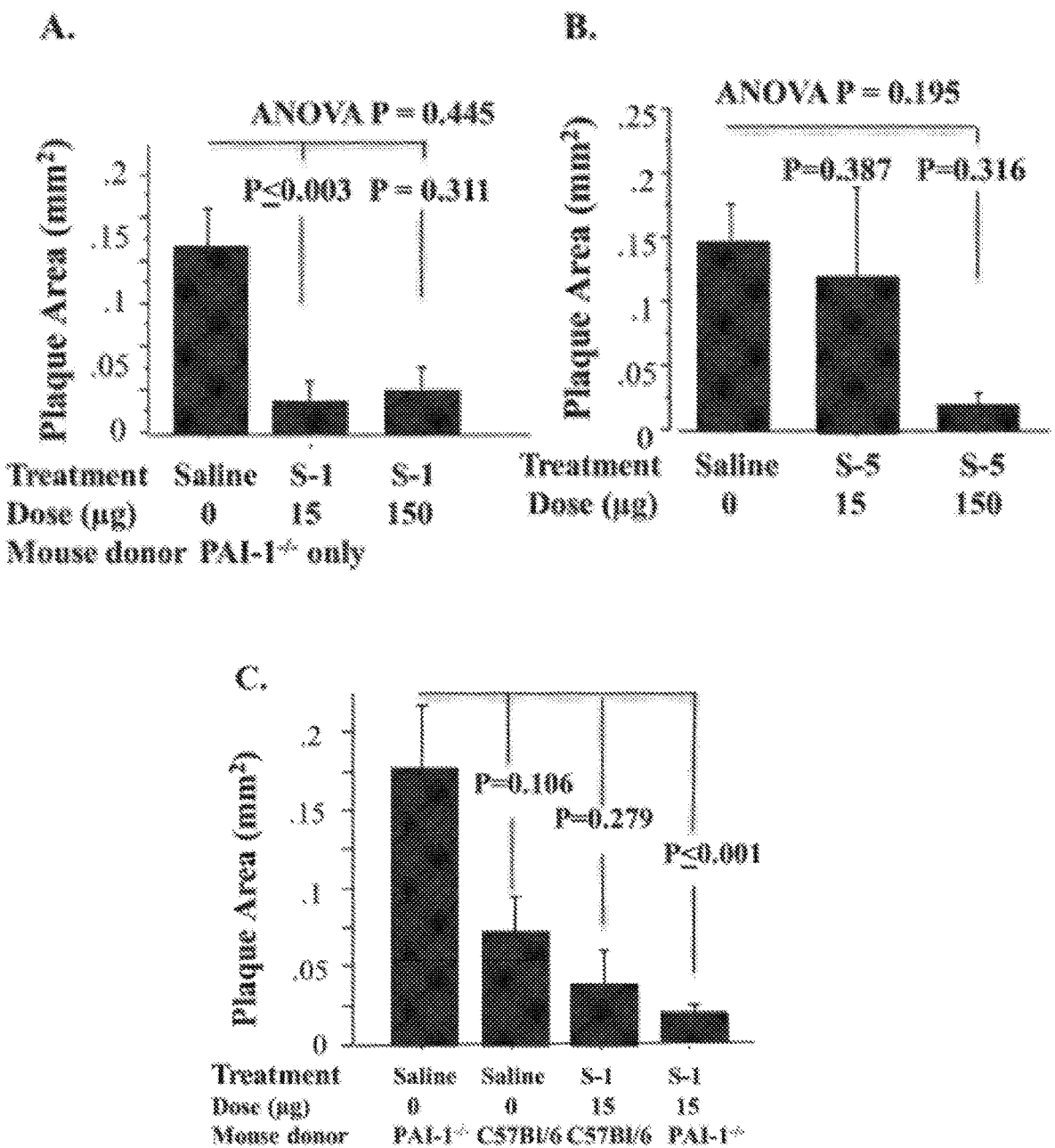
Figure 10D:
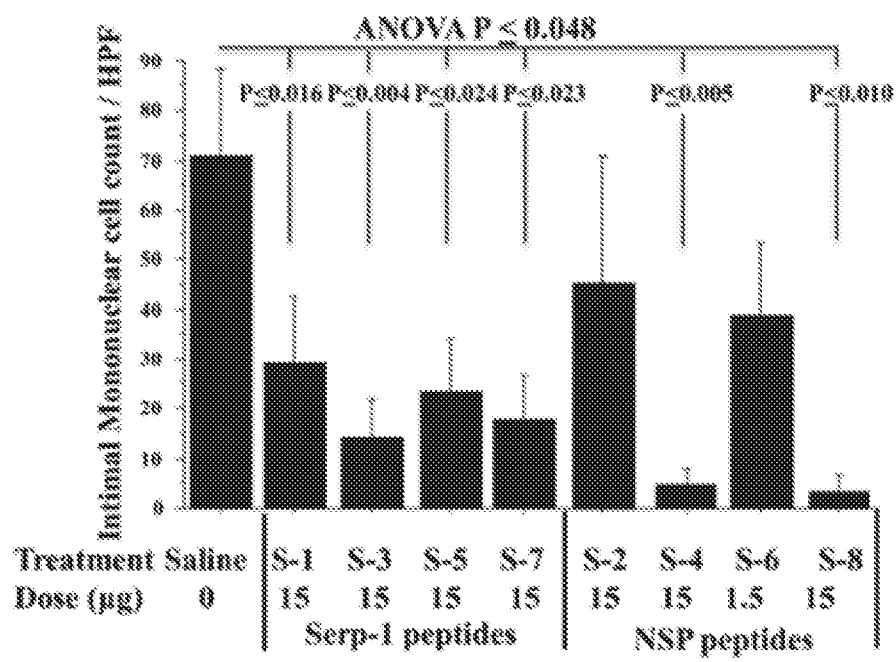
Figure 10E:
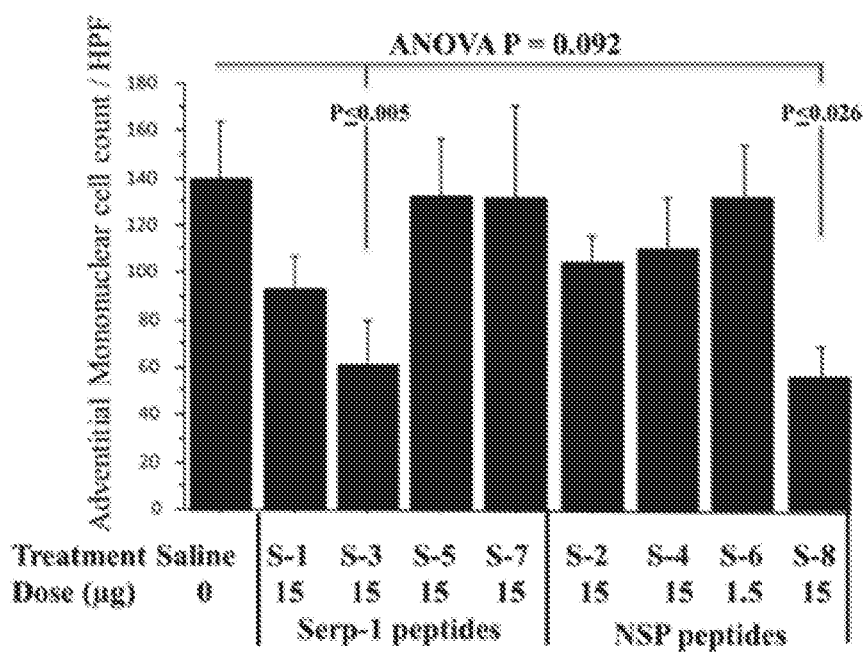

FIGS. 10A-10E show serpin peptide dose titration, effects on inflammatory mononuclear cell counts and differential effects in PAI-1 deficient aorta. FIG. 10A-B shows the titration curves for Serp-1 peptides S-1 (FIG. 10A) and S-5 (FIG. 10B) peptide treatments, respectively. S-1 peptide significantly reduced plaque in PAI-1−/− aortic allografts, and displayed a trend toward reduced plaque in C57BL/6 WT aortic allografts (FIG. 10C). FIGS. 10D-10E show counts of invading mononuclear cells (monocyte/macrophage and T cells at 28 days in intimal and adventitial layers, respectively.

Figures 11A, 11B:
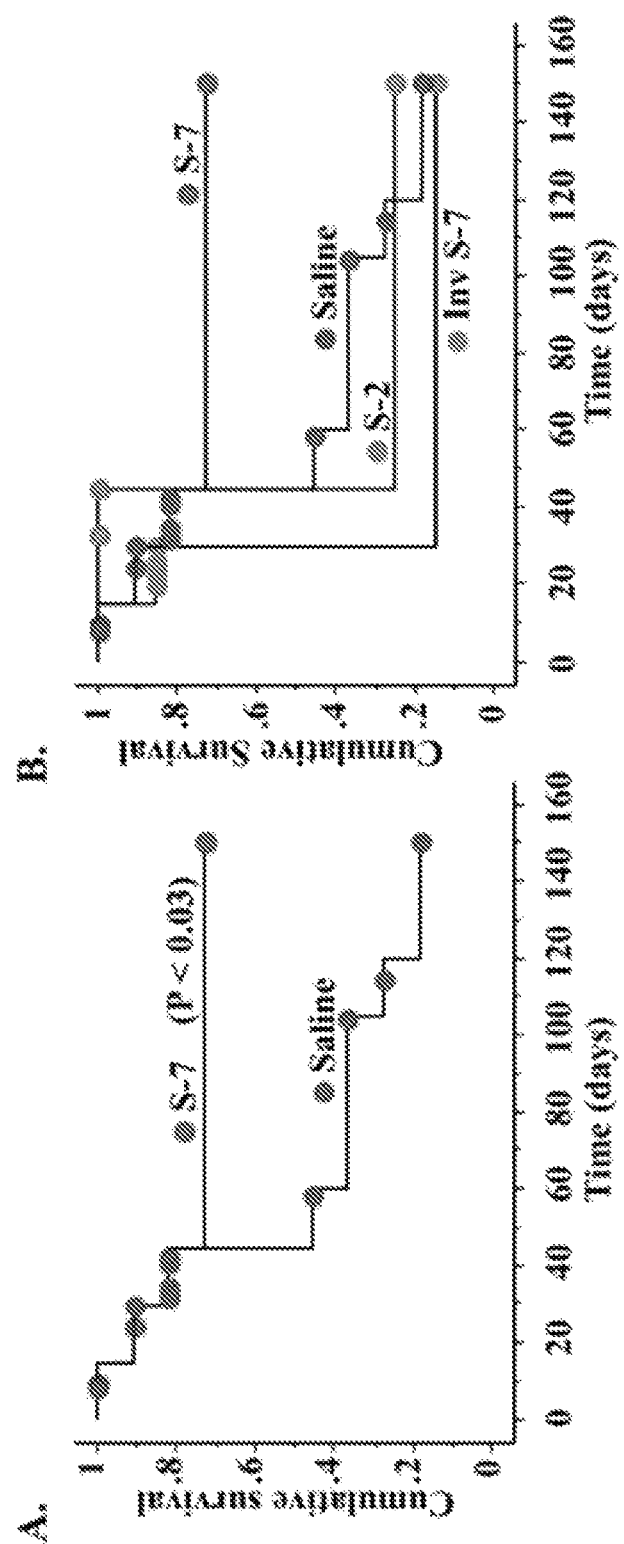

FIGS. 11A-11B show that serpin peptide S-7 improves survival in a lethal MHV68 vasculitis model. FIG. 11A shows Kaplan Meier survival curves demonstrate a significantly prolonged survival with S-7 treatment ($P \leq 0.03$). FIG. 11B shows that, in contrast, inverse S-7 peptide sequence and the S-2 peptide did not improve survival.

DETAILED DESCRIPTION

Many modifications and other embodiments of the present disclosure set forth herein will come to mind to one skilled in the art to which this disclosure pertains having the benefit of the teachings presented in the foregoing descriptions and the associated drawings. Therefore, it is to be understood that the present disclosure is not to be limited to the specific embodiments disclosed and that modifications and other embodiments are intended to be included within the scope of the appended claims. Although specific terms are employed herein, they are used in a generic and descriptive sense only and not for purposes of limitation.

Before the present compositions and methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

Moreover, it is to be understood that unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is in no way intended that an order be inferred, in any respect. This holds for any possible non-express basis for interpretation, including matters of logic with respect to arrangement of steps or operational flow, plain meaning derived from grammatical organization or punctuation, and the number or type of aspects described in the specification.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

As used in the specification and in the claims, the term "comprising" can include the aspects of "consisting of" and "consisting essentially of."

As used in the specification and the appended claims, the singular forms "a," "an" and "the" include plural referents unless the context clearly dictates otherwise.

The word "or" as used herein means any one member of a particular list and also includes any combination of members of that list.

Ranges can be expressed herein as from "about" or "approximately" one particular value, and/or to "about" or "approximately" another particular value. When such a range is expressed, a further aspect includes from the one particular value and/or to the other particular value. Similarly, when values are expressed as approximations, by use of the antecedent "about," or "approximately," it will be understood that the particular value forms a further aspect. It will be further understood that the endpoints of each of the ranges are significant both in relation to the other endpoint and independently of the other endpoint. It is also understood that there are a number of values disclosed herein and that each value is also herein disclosed as "about" that particular value in addition to the value itself. For example, if the value "10" is disclosed, then "about 10" is also disclosed. It is also understood that each unit between two particular units is also disclosed. For example, if 10 and 15 are disclosed, then 11, 12, 13, and 14 are also disclosed.

As used herein, the terms "optional" or "optionally" mean that the subsequently described event or circumstance may or may not occur and that the description includes instances where said event or circumstance occurs and instances where it does not.

As used herein, the term "polypeptide" refers to any peptide, oligopeptide, polypeptide, gene product, expression product, or protein. A polypeptide is comprised of consecutive amino acids. The term "polypeptide" encompasses naturally occurring or synthetic molecules. As used herein, the term "amino acid sequence" refers to a list of abbreviations, letters, characters or words representing amino acid residues.

As used herein, the term "subject" refers to the target of administration, e.g., a human. Thus, the subject of the disclosed methods can be a vertebrate, such as a mammal, a fish, a bird, a reptile, or an amphibian. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.). In one aspect, a subject is a mammal. In another aspect, a subject is a human. The term does not denote a particular age or sex. Thus, adult, child, adolescent and newborn subjects, as well as fetuses, whether male or female, are intended to be covered.

As used herein, the term "patient" refers to a subject afflicted with a disease or disorder. The term "patient" includes human and veterinary subjects. In some aspects of the disclosed methods, the "patient" has been diagnosed with a need for treatment prior to the administering step.

Serine protease inhibitors, or serpins, are ubiquitous, complex, and highly active regulatory molecules that effectively control multiple coagulation, inflammatory, and neuroendocrine pathways. The amino acid sequence in the reactive center loop (RCL) of serpins can act as bait for target serine proteases initiating structural changes in the serpin/protease complex and culminating in suicide inhibition (Silverman et al., (2001) J Biol Chem 276: 33293-33296; Law et al, (2006) Genome Biol 7: 216; and Gooptu and Lomas (2009) Annu Rev Biochem 78: 147-176). While the amino acid residues in the RCL provide target P1-P1' sequences, referred to as a scissile bond, serpins also require the greater part of the protein structure to function with endogenous serpin/protease inhibitory activity (Lucas et al., (2009) Adv Exp Med Biol 666: 132-156; and Sutherland et al., (2007) Thromb Haemost 98: 1014-1023). Serpin peptides derived during protein metabolism, however, may act to extend serpin activity beyond the initial suicide inhibitory function, both increasing and decreasing responses (Zhou et al., (2010) Nature 468: 108-111; Jia et al., (2012) Bioorg Med Chem Lett 22: 2393-2395; Kalle et al., (2013) J Immunol 190: 6303-6310; and Shmueli et al., (2013) Biomaterials 34: 7544-7551). Previous studies have shown significant and prolonged anti-inflammatory functions detected with myxomavirus-derived, Serp-1 (Lucas et al., (1996) Circulation 94: 2890-2900; Viswanathan et al., (2006) Thromb Haemost 95: 499-510; and Chen et al., (2013) Antimicrob Agents Chemother 57: 4114-4127), and mammalian serpin, neuroserpin (NSP), after single dose injections of purified proteins in animal models of vascular disease (Munuswamy-Ramanujam et al., (2010) Thromb Haemost 103: 545-555). As disclosed herein, serpin-derived peptides produced by protease cleavage of the RCL sequence during natural proteolytic metabolism of Serp-1 or NSP extend serpin activity, for example, by increasing anti-inflammatory activity after serpin-protease complex formation.

The presence of R (Arg), RN (Arg-Asn), or RNL (Arg-Asn-Leu) in the serpin-derived peptides disclosed herein is associated with anti-inflammatory and anti-atherogenic activity. A high proportion of active peptides contained an RN, RNL or R alone in the sequence. These active peptides may act to extend the natural lifespan of serpin inhibitory functions. In contrast, one peptide lacking R or RN, which had a markedly negative charge and hydrophobicity (S-6) was highly active, causing early local allograft thrombosis, but even at safe low doses did not have anti-inflammatory nor anti-atherogenic activity. This peptide was derived from NSP and may, thus, be postulated to extend the anti-thrombolytic, e.g. pro-thrombotic functions, of NSP. S-6 has clot formation activity and prevents bleeding.

Serpins are suicide inhibitors that form 1:1 stoichiometric complexes. For example, the protease cleaves the serpin RCL P1-P1' scissile bond thereby forming a complex with the serpin, such that both the serpin and the protease lose function after binding (Silverman G A, et al. (2001) J Biol Chem 276: 33293-33296; Lucas A, et al. (2009) Adv Exp Med Biol 666: 132-156; and van Gent D, et al. (2003) Int J Biochem Cell Biol 35: 1536-1547). The active serpin-derived peptides disclosed herein can represent a class of anti-inflammatory peptides similar to the highly active expanding classes of defensin peptides.

Plasminogen activator inhibitor-1 (PAI-1; SERPIN E1) and anti-thrombin III (AT, SERPIN C1) are among the most highly active mammalian serpins that regulate thrombolytic and thrombotic protease pathways. Other mammalian serpins include collagen or elastin degrading enzymes such as alpha-1 anti-chymotrypsin. Serpins are found throughout evolution and highly active serpins are expressed by viruses, such as poxviruses, providing a defense against host immune reactions to the virus (Kalle et al., (2013) J Immunol 190: 6303-6310; and Chen et al., (2011) Methods Enzymol 499: 301-329).

Serp-1 is a secreted myxomavirus-derived protein that binds and inhibits urokinase- and tissue-type plasminogen activators (uPA and tPA, respectively), plasmin, and factor X (fXa) with demonstrated inhibition of plaque growth and organ scarring in mouse, rat, and rabbit balloon angioplasty induced neointimal plaque growth and in rodent transplant models (Chen et al., (2013) Antimicrob Agents Chemother 57: 4114-4127). Earlier studies have demonstrated that administration of the purified Serp-1 protein as a single bolus infusion dose immediately after aortic allograft transplant significantly reduced plaque growth and inflammatory cell invasion at 4 weeks follow up (Jiang et al., (2007 Transplantation 84: 1158-1167). Serp-1 administration after cardiac or renal (Dai et al., (2003) J Biol Chem 278: 18563-18572; Jiang et al., (2007) Transplantation 84: 1158-1167; and Chen et al., (2011) Methods Enzymol 499: 301-329) allograft transplants along with the immunosuppressant cyclosporine, significantly reduced vascular plaque growth and scarring in rodents when compared to cyclosporine treatment alone. NSP, a mammalian serpin that binds tPA and uPA with a greater predilection for tPA, has been reported to reduce cerebral infarct size in mouse models (Dai et al., (1997) Brain Res 1015: 175-180) and also to reduce inflammation and vascular plaque growth in mouse models of aortic allograft transplant (Munuswamy-Ramanujam et al., (2010) Thromb Haemost 103: 545-555; and Chen et al., (2011) Methods Enzymol 499: 301-329). In a Phase 2a clinical trial, Serp-1 reduced early markers of myocardial damage in patients with acute unstable angina after stent implantation (Tardif et al., (2010) Circ Cardiovasc Interv 3: 543-548). Its therapeutic use may, however, be limited because of its short plasma half-life (20 minutes to 1 hour).

The serpins, Serp-1 and NSP, have been previously demonstrated to possess potent inhibitory activity, preventing inflammatory cell activation and late vascular plaque growth after single dose infusions at the time of arterial injury or transplant (Dai E, et al. (2003) J Biol Chem 278: 18563-18572; Lucas A, et al. (1996) Circulation 94: 2890-2900; and Munuswamy-Ramanujam G, et al. (2010) Thromb Haemost 103: 545-555). Serp-1 additionally reduced inflammation and lung consolidation and improved survival in mouse models of lethal viral sepsis while NSP was inactive in this model (Chen H, et al. (2013) Antimicrob Agents Chemother 57: 4114-4127). The prolonged efficacy of single doses of Serp-1 and NSP would suggest a potential for additional functions. This prolonged activity for a serpin, with a presumed limited lifespan, suggests a mechanism that would extend functions such as inhibition of pivotal central regulatory steps, modification of cell activation and gene expression, or perhaps through active proteolytic metabolites such as the serpin-derived peptides disclosed herein. The serpin reactive center loop and specifically the P1-P1' scissile bond, which is cleaved by serine proteases, represents a natural peptide processing site for serpins.

Disclosed herein are serpin reactive center loop-derived peptides. These RCL (reactive center loop) peptides have anti-inflammatory, anti-atherogenic and, in some cases, pro-thrombotic functions that can extend serpin regulatory activity, providing a therapeutic approach for the treatment and/or prevention of lethal hemorrhagic infections and lethal sepsis.

Serpin-Derived Peptides:

Peptides, or polypeptides, described herein are derived from Serp-1 and NSP in the serpin reactive center loop and can extend serpin-mediated activity. These peptides are referred to herein as "serpin peptides," "serpin-derived peptides," "RCL peptides" and "polypeptides derived from a reactive site loop of a serine protease inhibitor." The serpin-derived peptides disclosed herein can be used in compositions and methods as disclosed herein.

Accordingly, in some embodiments, the compositions of the present disclosure comprise a serpin-derived peptide or a biologically active variant thereof that has an amino acid sequence of IPRNAL (S-1; SEQ ID NO:1); ISRMAV (S-2; SEQ ID NO:2); RNAL (S-3; SEQ ID NO:3); IAISRM (S-4; SEQ ID NO:4); TAIVANKPF (S-5; SEQ ID NO:5); EVNEEGSEAAAVSGM (S-6; SEQ ID NO:6); GTTASSD-TAITLIPR (S-7; SEQ ID NO:7) or MAVLYPQVIVDHPFF-FLIRNR (S-8; SEQ ID NO:8). Serp-1-derived RCL peptides include amino acid sequences S-1, S-3, S5 and S-7 (SEQ ID NOs: 1, 3, 5 and 7, respectively). NSP-derived RCL peptides include amino acid sequences S-2, S-4, S-6 and S-8 (SEQ ID NOs: 2, 4, 6 and 8, respectively). In some aspects, the serpin-derived peptides are derived from Serp-1, wherein the Serp-1 is derived from a Myxoma-virus. In other aspects, the serpin-derived peptides are derived from the mammalian NSP.

In various embodiments, the polypeptides or variants as described herein are serpin-derived peptides that can inhibit one or more serine proteases. The serine proteases can be thrombolytic or thrombotic. Further, the peptides described herein, can reduce inflammation.

With respect to length, the serpin-derived peptides can have about, or less than about, 25 amino acids, or 21 amino acids, or 4 amino acid residues. With respect to sequence, serpin-derived peptides can have a sequence found in a reactive cleavage loop or a fragment thereof. A portion or fragment of a reactive loop can be as short as 4-25 amino acid residues (e.g., 4, 5, 6, 7, or 8 contiguous residues). These RCL peptides can bind and inhibit proteases, such as uA or thrombin, or conversely, they can bind and inhibit other serpins by inserting into the normal cleaved serpin insertion site for cleaved RCL loops. A biologically active fragment of a serpin-derived peptide can be at least or about 80% identical (e.g., at least or about 85%, 90%, 95%, 98%, or 99% identical) to a corresponding portion of an endogenous serpin protein or serpin-derived peptide.

It is known that the Serp-1 RCL scissile P1-P1' bond sequence is Arg-Asn (RN). Accordingly, in some aspects, the polypeptides (i.e., the serpin-derived peptides) as described herein contain an Arg-Asn amino acid sequence or at least one Arg amino acid residue. Further, when the Serp-1 RCL P1-P1' RN sequence was mutated to Ala-Ala (AA) the anti-atherogenic function was lost. Beneficial effects, however, were detectable weeks to months later in animal models, suggesting extended function potentially produced by active metabolites or altered gene expression in early response cells in the innate immune system.

Serpin-derived peptides disclosed herein were designed and synthesized based on predicted (using PeptideCutter utility of Expasy program (the Expert Protein Analysis System)) metabolites derived from natural proteolysis of either Serp-1 or NSP RCL sequences. Serpins are expressed by pox viruses, including cow pox (vaccinia) and rabbit pox (myxoma). Alternatively, or in addition, one can use other species which have serpin proteins or proteins that are functionally and structurally similar to serpins. In some instances, the sequences or biologically active variants thereof, derived from one virus or species can be identical to those derived from another species. A corresponding sequence will be apparent to one of ordinary skill in the art.

The sequences disclosed herein can be modified at, for example, either the amino terminus, the carboxy terminus, or both. For example, the sequences can include at least two cysteine residues, one or both of which are, optionally, at the C-terminal or N-terminal of the serpin-derived peptide. In an aspect, the serpin-derived peptide can include a naturally occurring serpin-derived sequence. For example, a serpin-derived peptide can include a naturally occurring serpin-derived sequence having at or near each of the C- and N-termini, a cysteine residue. The serpin-derived sequence can be cyclized by formation of a disulfide bond between these two cysteine residues (or, more generally, between two of the at least two cysteine residues present at the terminal regions). While the peptides of the present disclosure can be linear or cyclic, cyclic peptides generally have an advantage over linear peptides in that their cyclic structure is more rigid and hence their biological activity can be higher than that of the corresponding linear peptide. Any method for cyclizing peptides can be applied to the serpin-derived peptides or fragments described herein.

Alternatively, or in addition, the serpin-derived peptides can also include a substituent at the amino-terminus or carboxy-terminus. The substituent can be an acyl group or a substituted or unsubstituted amine group (e.g., the substituent at the N-terminus can be an acyl group and the C-terminus can be amidated with a substituted or unsubstituted amine group (e.g., an amino group having one, two, or three substituents, which may be the same or different)). The amine group can be a lower alkyl (e.g., an alkyl having 1-4 carbons). The acyl group can be a lower acyl group (e.g., an acyl group having up to four carbon atoms), especially an acetyl group.

As noted, the serpin-derived peptides can vary in length and can be or can include contiguous amino acid residues that naturally occur in Serp-1 or NSP or that vary to a certain degree from a naturally occurring Serp-1 or NSP sequence (but retain a biological activity). Where the fragments include, at their N-terminus or C-terminus (or both), amino acid residues that are not naturally found in Serp-1 or NSP, the additional sequence(s) can be about 200 amino acid residues long, and these residues can be divided evenly or unevenly between the N- and C-termini. For example, both the N- and C-termini can include about 10, 20, 30, 40, 50, 60, 70, 80, 90, or 100 amino acid residues. Alternatively, one terminus can include about 10, 20, 30, 40, 50, 60, 70, 80, 90, 100, 110, 120, 130, 140, 20 150, 160, 170, 180, 190, or 200 residues, and one terminus can include none (e.g., it can terminate in an amino acid sequence identical to a naturally occurring Serp-1 or NSP sequence).

More specifically, the N- or C-termini can include 1 to about 100 (e.g., 1, 2, 3, 4, 5, 6, 7, 8, 9, 10, 15, 20, 25, 30, 40, 50, 60, 70, 80, 90, or 100) amino acid residues that are positively charged (e.g., basic amino acid residues such as arginine, histidine, and/or lysine residues); 1 to about 100 amino acid residues that are negatively charged (e.g., acidic amino acid residues such as aspartic acid or glutamic acid residues); 1 to about 100 glycine residues; 1 to about 100 hydrophobic amino acid residues (e.g., hydrophobic aliphatic residues such as alanine, leucine, isoleucine or valine or hydrophobic aromatic residues such as phenylalanine, tryptophan or tyrosine); or 1 to about 100 (e.g., 1-4) cysteine residues. Where biologically active variants of a Serp-1 or NSP fragment are used, the variant can vary by substitution of one or more amino acid residues within these groups. The variants can include a conservative amino acid substitution.

The fragments of Serp-1 or NSP or the serpin-derived peptides can also be modified in order to improve absorption, including for example, an addition of sugar residues to enhance transport across the blood-brain barrier.

The serpin-derived peptides can comprise modified amino acids, such as those known to one of ordinary skill in the art. Disclosed peptides can include natural, unnatural, or non-amino acid residues. Synthetic peptides, for example, include those with modified amino acids or other moieties in place of an amino acid. The inclusion of unnatural or non-amino acids can be made to stabilize the peptide, block metabolization, or to create a conformational change in the peptide which would increase its effectiveness. Preferably, the amino acids of the peptides are in the L-orientation, although amino acids or peptides in the D-orientation can also be used, as can be peptides in the reverse orientation.

The serpin-derived peptides or fragments thereof, including the variant forms described herein, can further include a heterologous polypeptide (i.e., a polypeptide having a sequence that does not appear in Serp-1 or NSP). The heterologous polypeptide can be a polypeptide that increases the circulating half-life of the fragment of Serp-1 or NSP or the serpin-derived peptides to which it is attached (e.g., fused, as in a fusion protein). The heterologous polypeptide can be an albumin (e.g., a human serum albumin or a portion thereof).

Any of the serpin-derived peptides or fragments or variants thereof in the present compositions can be one of a plurality present in multimeric form (e.g., as a dimer). The multimeric form can also include one or more types of serpin-derived peptides or fragments or variants thereof wherein the two or more serpin-derived peptides are identical or non-identical.

The serpin-derived peptides or fragments thereof can be contained within physiologically acceptable compositions or they can be contained within compositions that are not suitable for administration to a living being (e.g., concentrated stocks or frozen or lyophilized compositions). The physiologically acceptable compositions can be pharmaceutical compositions, and methods of treating patients are described further below. The terms "physiologically acceptable" or pharmaceutically acceptable" are used herein to mean any formulation which is safe, and provides the appropriate delivery for the desired route of administration of an effective amount of a composition described herein.

In an aspect, the present disclosure also encompasses nucleic acid molecules that encode the serpin-derived peptides or fragments thereof described herein. Nucleic acids can encode expression vectors.

In an aspect, a composition disclosed herein comprises nucleic acid molecules that encode the serpin-derived peptides or fragments thereof disclosed herein in an expression construct or in a single or separate cassette. Disclosed herein is an expression construct capable of expressing serpin-derived peptides or fragments thereof.

A disclosed expression cassette can include 5' and 3' regulatory sequences operably linked to a polynucleotide disclosed herein. "Operably linked" is intended to mean a functional linkage between two or more elements. For example, an operable linkage between a polynucleotide disclosed herein and a regulatory sequence (e.g., a promoter) is a functional link that allows for expression of a polynucleotide disclosed herein. Operably linked elements can be contiguous or non-contiguous. When used to refer to the joining of two protein coding regions, by operably linked is intended that the coding regions are in the same reading frame. An expression cassette may further comprise at least one additional polynucleotide to be co-transformed into the organism. Alternatively, one or more polypeptide(s) can be expressed on one or more expression cassettes. Expression cassettes can be provided with a plurality of restriction sites and/or recombination sites for insertion of the polynucleotide to be under the transcriptional regulation of the regulatory regions.

The regulatory regions (i.e., promoters, transcriptional regulatory regions, and translational termination regions) and/or the polynucleotides disclosed herein can be native/analogous to the host cell or to each other. Alternatively, the regulatory regions and/or the polynucleotide employed in the invention can be heterologous to the host cell or to each other. As used herein, "heterologous" in reference to a sequence is a sequence that originates from a foreign species, or, if from the same species, is substantially modified from its native form in composition and/or genomic locus by deliberate human intervention. For example, a promoter operably linked to a heterologous polynucleotide is from a species different from the species from which the polynucleotide was derived, or, if from the same/analogous species, one or both are substantially modified from their original form and/or genomic locus, or the promoter is not the native promoter for the operably linked polynucleotide. As used herein, a chimeric gene comprises a coding sequence operably linked to a transcription initiation region that is heterologous to the coding sequence.

In preparing the expression cassette, the various DNA fragments can be manipulated, so as to provide for the DNA sequences in the proper orientation and, as appropriate, in the proper reading frame. Toward this end, adapters or linkers can be employed to join the DNA fragments or other manipulations can be involved to provide for convenient restriction sites, removal of superfluous DNA, removal of restriction sites, or the like. For this purpose, in vitro mutagenesis, primer repair, restriction, annealing, resubstitutions, e.g., transitions and transversions, can be involved.

A number of promoters can be used in the practice of the invention. The promoters can be selected based on the desired outcome. The choice of promoters depends on several factors including but not limited to efficiency, selectability, inducibility, desired expression level, and cell- or tissue-preferential expression. The nucleic acids can be combined with constitutive, tissue-preferred, inducible, or other promoters for expression in the host organism. One skilled in the art is capable of appropriately selecting and positioning promoters and other regulatory regions relative to the coding sequence.

Manufacturing Peptides:

Synthesis of non-peptide compounds that mimic peptide sequences is known in the art. Such non-peptide compounds that mimic serpin-derived peptides with anti-inflammatory activity and/or antiatherogenic or anti-sepsis activity are within the scope of the present disclosure.

The present disclosure also contemplates synthetic mimicking compounds that are multimeric by repeating the relevant serpin-derived peptide sequence. It is well-known in the art that peptides can be synthesized by linking an amino acid group to a carboxyl group that has been activated by reaction with a coupling agent, such as dicyclohexylcarbodiimide. The attack of a free amino group on the activated carboxyl leads to the formation of a peptide bond and the release of dicyclohexylurea. It can be necessary to protect potentially reactive groups other than the amino and carboxyl groups intended to react. For example, the α-amino group of the component containing the activated carboxyl group can be blocked with a tertbutyloxycarbonyl group. This protecting group can be subsequently removed by exposing the peptide to dilute acid, which leaves peptide bonds intact.

With this method, peptides can be readily synthesized by a solid phase method by adding amino acids stepwise to a growing peptide chain that is linked to an insoluble matrix, such as polystyrene beads. The carboxyl-terminal amino acid (with an amino protecting group) of the desired peptide sequence is first anchored to the polystyrene beads. The protecting group of the amino acid is then removed. The next amino acid (with the protecting group) is added with the coupling agent. This is followed by a washing cycle. The cycle is repeated as necessary.

The mimetics of the present disclosure are peptides having sequence homology to the disclosed serpin-derived peptides (including, but not limited to, peptides in which L-amino acids are replaced by their D-isomers). Techniques for evaluating sequence homology are known in the art.

The serpin-derived peptides disclosed herein and the mimetics described above can be synthesized using any known method, including tea-bag methodology or solid phase peptide synthesis procedures or using a commercially available automated synthesizer.

Pharmaceutical Compositions:

The pharmaceutical compositions described herein can be administered in any form by any effective route, including but not limited to, oral, parenteral (e.g., intravenous, intradermal, subcutaneous, intraperitoneal, intramuscular, inhalation, transdermal (topical) and transmucosal administration), etc. They can be administered alone, or in combination with any ingredient(s), active or inactive. Solutions or suspensions used for parenteral administration can include: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The composition can be aliquoted or packaged in ampules, disposable syringes, single or multiple dose vials made of glass or plastic, bottles, and the like, and such packaged forms, along with instructions for use, are within the scope of the present disclosure.

Pharmaceutical compositions adapted for injection include, for example, sterile aqueous solutions (where water soluble) or dispersions and sterile powders for the extemporaneous preparation of sterile injectable solutions or dispersion. For intravenous administration, suitable carriers include, for example, physiological saline, bacteriostatic water, and phosphate buffered saline (PBS). The compositions prepared for administration should be sterile and should be fluid or convertible to a fluid at least sufficient for easy loading into a syringe. The composition and/or nucleic acid constructs should be stable under the conditions of manufacture and storage and should be preserved against the contaminating action of microorganisms such as bacteria and fungi. Preservatives against microorganisms can include various antibacterial and antifungal agents, for example, parabens, chlorobutanol, phenol, ascorbic acid, thimerosal, and the like.

The carrier can be a solvent or dispersion medium containing, for example, water, ethanol, polyol (for example, glycerol, propylene glycol, and liquid polyetheylene glycol, and the like), and suitable mixtures thereof. Fluidity can be maintained, for example, by the use of a coating such as lecithin, by the maintenance of the required particle size in the case of dispersions and by the use of surfactants.

In some instances, it may be desirable for the composition to be isotonic to blood. This can be accomplished using various isotonic agents, for example, sugars, polyalcohols such as manitol, sorbitol, sodium chloride in the composition.

Delayed or extended absorption of the injectable compositions can be achieved by including in the composition an agent which delays absorption, for example, aluminum monostearate and gelatin, or by coating micro- or nano-particles of active agent in the composition with materials that delayed or extended release of components.

Sterile injectable solutions can be prepared, for example, by solubilizing or suspending the active compound in the required amount in an appropriate solvent with one or a combination of additional ingredients. Typically, creation of such solution or suspension is followed by sterile filtration. Generally, dispersions are prepared by incorporating the active compound into a sterile vehicle which contains a basic dispersion medium and the other desired ingredients. In the case of sterile powders for the preparation of sterile injectable solutions, the preparation is dried, e.g., by vacuum drying and/or freeze-drying.

Liposomal suspensions can also be used to prepare pharmaceutical compositions. These can be prepared according to methods known to those skilled in the art.

Oral or parenteral compositions can be formulated in dosage units for ease of administration and uniformity of dosage. "Dosage unit form" as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the disclosure are dictated by and directly dependent on the unique characteristics of the active compound and the particular therapeutic effect to be achieved, and the limitations inherent in the art of compounding such an active compound for the treatment of individuals.

The nucleic acid molecules can be formulated in physiologically acceptable compositions for administration.

The present disclosure also features vectors that include nucleic acid constructs. Vectors can be, for example, viral, plasmid, cosmid, or artificial chromosome vectors.

Plasmids are generally circular, dsDNA elements that include one or more cloning sites for insertion of selected DNA sequences, e.g., coding sequences.

Viral vectors (e.g., retroviruses, lentiviruses, adenoviruses and adeno-associated viruses) can be used. Techniques and procedures for producing recombinant retroviruses and for infecting cells in vitro or in vivo with such viruses are well-known in the art.

Vectors as described herein can advantageously include a serpin-derived peptide of the disclosure. The design of a particular expression vector can depend on the choice of the host cell to be transformed, the level of expression of protein desired, etc. The expression vectors of the present disclosure can be introduced into host cells to thereby produce proteins or peptides, including fusion proteins or peptides, encoded by nucleic acids as described herein.

Vectors described herein can be introduced into cells or tissues by any one of a variety of known methods within the art. The methods include, for example, stable or transient transfection, lipofection, electroporation and infection with recombinant viral vectors. The term "transfecting" or "transfection" encompasses all conventional techniques for introducing nucleic acid into host cells, including calcium phosphate coprecipitation, DEAE-dextran-mediated transfection, lipofection, electroporation and microinjection.

Compositions of the serpin-derived peptides described herein can be provided together with physiologically tolerable liquid, gel or solid carriers, diluents, adjuvants and excipients.

Serpin-derived peptides described herein can be mixed with diluents or excipients which are physiological tolerable and compatible. Suitable diluents and excipients include, but are not limited to water, saline, dextrose, glycerol, or the like, and any combinations thereof. In addition, if desired, the compositions can contain small amounts of auxiliary substances such as wetting or emulsifying agents, stabilizing or pH buffering agents.

One of ordinary skill in the art will appreciate that the individual components of the present disclosure can change depending on the physical and chemical qualities needed for the pharmaceutical compositions in a given process and/or application to which the pharmaceutical compositions are applied.

Other Uses

Methods of Treatment:

The present disclosure features methods of treating hemorrhagic viral or bacterial infections and viral or bacterial sepsis that is a result of a DNA or RNA virus or bacteria. The serpin-derived peptides described herein can also be used to prevent allograft rejection and treat and/or prevent allograft vascular disease. The pharmaceutical compositions described above can be formulated to include a therapeutically effective amount of one or more of the serpin-derived peptides or nucleic acids encoding the serpin-derived peptides disclosed herein. Therapeutic administration also includes prophylactic applications. A physician can choose a prophylactic administration wherein the subject (e.g., individual or patient) has an increased susceptibility (e.g., weakened immune system), a clinically determined predisposition or an increased risk to a hemorrhagic infection or sepsis. In therapeutic applications, compositions are administered to a subject (e.g., a human patient) already suffering from, for example, a hemorrhagic infection or sepsis in an amount sufficient to at least partially improve one or more signs or symptoms or to inhibit the progression of (and preferably arrest) the symptoms of the condition, its complications, and consequences. Additionally, compositions can be administered to a patient undergoing a cardiac allograft transplant. As used herein, the term "therapeutically effective amount" of a physiological or pharmaceutical composition refers to the amount that provides a treatment that delays, prevents one or more symptoms associated with a hemorrhagic infection or sepsis or even cures or ameliorates the infection or condition. Recovery can be accelerated in an individual who has been treated.

The therapeutically effective amount of the compositions described herein and used in the methods disclosed herein applied to humans (e.g., patients, individuals, subjects) can be determined by one of ordinary skill in the art with consideration of individual differences in age, weight, and previous exposure to DNA virus or RNA virus or bacteria.

The present methods are effective for targeting thrombotic and thrombolytic pathways; reducing inflammation, lung consolidation, arterial inflammatory vasculitis and even colon dilatations well as bleeding (e.g., excess bleeding), and reducing clot formation.

The methods of the present disclosure also include methods for treating a patient who has or is at risk for a hemorrhagic viral, bacterial or fungal infection. Further, the methods disclosed herein can include the treatment of transplant vascular disease including but not limited to cardiac allograft transplant in a patient. These methods can be carried out by, for example, administering to the patient a therapeutically effective amount of a pharmaceutical composition comprising a serpin-derived peptide, or a biologically active variant or fragment thereof, as described herein. The methods can also include a step of identifying a patient in need of treatment (e.g., fever, severe headache, unexplained hemorrhage (bleeding or bruising)) and/or a patient who is at risk for a hemorrhagic viral infection (e.g., travel to an endemic country). The patient's symptoms (e.g., fever, severe headache, hemorrhage) can be associated with exposure to Ebola virus or Marburg virus.

The term "hemorrhage" or "hemorrhagic" is used herein to mean blood that is outside of or has escaped the circulatory system. An external hemorrhage is visible bleeding outside of the body and an internal hemorrhage shows little or no sign of bleeding. The classification scheme of a hemorrhage denotes the amount of or degree or severity of the blood loss ranging from 15% of total blood volume Class I (or a Grade 1), 15-30% (Class II; Grade 2); 30-40% of circulating blood (Class III; Grade 3) to more than 40% of circulating blood volume (Class IV; Grade 4).

In addition to administration of the compositions described herein, the patient can receive a second type of treatment for other infections. Examples of agents that can be used singly or in combination with the compositions described herein include but are not limited to anti-inflammatories (e.g. aspirin and interleukin 10), antibiotics, antivirals, clot inhibitors (e.g., heparin, anti-thrombin III, activated protein C, tissue factor pathway inhibitor, and thrombomodulin), agents that block hemorrhage (e.g., factor VII), surgery, or any other treatment for sepsis or hemorrhage.

Other methods of the present disclosure are methods for treating a patient who has lethal sepsis (bacterial, viral or fungal), reducing inflammation and/or hemorrhage. The methods include a step of administering to a patient a therapeutically effective amount of a pharmaceutical composition comprising a serpin-derived peptide, or a biologically active variant or fragment thereof, as described herein. The methods can also include a step to identify a patient in need of such treatment. Such patients include those who are suffering from a DNA or RNA virus, and those that have been exposed to or have a hemorrhagic viral infection caused by exposure to a filovirus (e.g., Ebola virus or Marburg virus). The filovirus genus includes Zaire Ebola virus, Sudan Ebola virus, Reston Ebola virus, Cote d'l voire Ebola virus and Marburg virus.

The terms "treating" or "preventing" are used herein to mean the delay of the onset of one or more of the signs and/or symptoms, reducing the duration and/or severity of one or more of the signs or symptoms, reducing the number of symptoms, reducing the incidence of disease-related or infection-related symptoms, reducing the latency of symptoms, ameliorating symptoms, reducing any secondary symptoms, reducing any secondary infections, preventing relapse to a disease or infection, expediting remission, inducing remission, augmenting remission, speeding recovery, or increasing efficacy of or decreasing resistance to alternative therapeutics.

Further, the method of the present disclosure can include reducing one or more of the symptoms in a patient associated with sepsis or a hemorrhagic infection. For example, Marburg hemorrhagic fever is characterized by fever, abdominal pain, hemorrhage, shock and mortality. Other signs and symptoms include chills, headache, myalgia, maculopapular rash (generally appearing on the truck, e.g., chest, back, stomach), nausea, vomiting, chest pain, sore throat, diarrhea, jaundice, pancreatic, severe weight loss, delirium, shock, liver failure, and multi-organ dysfunction. The onset of one or more symptoms can be sudden, but they often appear after a 5 to 10 day incubation period. As the infection progresses, the additional symptoms emerge. Symptoms of Ebola, for instance, include fever, severe headache, muscle pain, weakness, fatigue, diarrhea, vomiting, abdominal pain (e.g., stomach pain), hemorrhage (bleeding or bruising). After exposure to the Ebola virus, one or more of the symptoms can present between about 2 to 21 days.

Individuals at risk of exposure to a filovirus include but are not limited to healthcare providers and other individuals (e.g., family members) that are in or have close contact with an individual previously exposed to a filovirus or presenting with one or more symptoms associated with an infection caused by a filovirus, for example, human patients or non-human primates that are infected with a filovirus; bats; or individuals traveling to and/or from endemic countries or areas.

The risk for exposure to a filovirus can be higher for individuals of particular occupations including veterinarians, hospital workers, laboratory or quarantine facility workers. In addition, the risk of exposure to a filovirus is increased for individuals traveling to endemic regions of Africa including but not limited to Uganda, South Africa, Republic of Congo, Ivory Coast, South Sudan, Gabon, and Democratic Republic of the Congo. Individuals that have come into contact with fruit bats, have visited or accessed caves or mines populated by fruit bats are at an increased risk for exposure to a filovirus.

The method of the present disclosure also include treating and/or reducing one or more of the symptoms in a patient associated with sepsis (e.g., bacterial or viral). Sepsis is defined as inflammation, a response by the immune system caused by an infection that affects the body as a whole. Common symptoms of sepsis include but are not limited to fever, increased heart rate, increased respiratory rate and confusion. Additional symptoms can be related to a specific type of infection (e.g., a cough associated with pneumonia). In cases of severe sepsis, the body's organs can become dysfunctional or fail. Organ failure is due to blood coagulation. Sepsis can be fatal.

Signs or symptoms of sepsis include but are not limited to fever, chills, impaired mental status, increased breathing or respiratory rate, changes in the temperature of the skin (e.g., warm or cold skin), abdominal pain, low blood pressure, bruising, bleeding and dysfunctions of blood coagulations. Bacterial sepsis can be associated with other conditions such as liver disease, gallbladder disease, colon disease, abscess, intestinal obstruction, pyelonephritis, intra- or perinephric abscess, renal calculi, urinary tract obstruction, acute prostatitis or abscess, peritonitis, pneumonia, empyema, endocarditis, abscess in the GI or GU tract, pelvis, respiratory tract, and vascular system.

The present disclosure also features methods of producing the serpin-derived peptides described herein; method of producing pharmaceutical compositions that include the serpin-derived peptides; and the use of these serpin-derived peptides and compositions in the treatment of an infection or a disease.

Therapeutically effective amounts of the serpin-derived peptides can be determined empirically by those of skill in the art. For example, either single or multiple administrations of the pharmaceutical compositions described herein can be carried out with dosage levels and the timing or pattern of administration being selected by the treating physician. The dose and administration schedule can be determined and adjusted based on the severity of the disease, signs and symptoms or condition in the subject. The signs and symptoms and the overall condition of the subject can be monitored throughout the course of treatment according to the methods commonly practiced by clinicians or other skilled healthcare professionals.

Kits:

Kits are within the scope of the present disclosure and can include any combination of the compositions described above and suitable instructions (whether written and/or provided as audio-, visual-, or audiovisual material). In one embodiment, the kit includes a pharmaceutical composition that is packaged along with instructions for use and, optionally, any device useful in manipulating the compositions in preparation for administration and/or in administering the compositions. The kits described herein can, for example, include one or more of: diluents, gloves, vials or other containers, pipettes, needles, syringes, tubing, stands, spatulas, sterile cloths or drapes, positive and/or negative controls, and the like.

EXAMPLES

Example 1: Chemical Characteristics and Primary Structure of Serpin Peptides

Eight peptides were examined representing predicted metabolites derived from natural proteolysis of either Serp-1 or NSP RCL sequences. The chemical characteristics of these peptide metabolites are provided in FIG. 1, together with the primary structure (Wimley Lab PepDraw, Tulane University, New Orleans La.). The pI (isoelectric point), hydrophobicity, and net charge varied. Of note, peptides S-1 (IPRNAL; SEQ ID NO: 1), S-3 (RNAL; SEQ ID NO: 3), S-5 (TAIVANKPF; SEQ ID NO: 5), S-2 (ISRMAV; SEQ ID NO: 2), S-4 (IAISRM; SEQ ID NO: 4) and S-8 (MAV-LYPQVIVDHPFFFLIRNR; SEQ ID NO: 8) all had predicted net positive (+1) charge while S-7 (GTTASSD-TAITLIPR; SEQ ID NO: 7) had predicted net 0 charge and S-6 (EVNEEGSEAAAVSGM; SEQ ID NO: 6), net negative (−4) charge. The pI for most peptides ranged from 6.42 to 11.11, but S-6 was an outlier with pI of 2.75. The hydrophobicity calculation was also similar for most peptides, with a range from +7.76 to +14.07; however, S-6 peptide was again an outlier with a calculated hydrophobicity of +26.40. The secondary structure was analyzed using the Online ExPasy site (see, http://www.expasy.org; Bloomsbury UK site). The RNAL (SEQ ID NO:3) sequence is predicted to form a helix while the other sequences are predicted to form either strands (AITLIPR; SEQ ID NO:9) or coil (GTTASSDT; SEQ ID NO:10). None of the RCL peptides had inhibitory activity for urokinase-type plasminogen activator (uPA) ((FIG. 2); FIG. 8A) or tissue-type plasminogen activator (tPA) (FIG. 8B) activity by chromogenic protease activity assay. Neither did any of the peptides inhibit the activity of plasmin or fXa (data not shown). On chromogenic assay, the serpin-derived RCL peptides did demonstrate inhibition of PAI-1. S-1, S-3, S-6, S-7 and S-8 demonstrated a trend toward greater inhibition of PAI-1 than S-2 and S-5 (FIG. 8C). ATIII was not significantly inhibited by the peptides (data not shown). The potential for these peptides to bind to and inhibit other serpins, plasminogen activator inhibitor-1 (PAI-1) and ATIII was also examined in silico and demonstrated potential for binding of S-7 to PAI-1 (data not shown).

FIG. 8D shows the molecular model of S-7 docked in the A-beta sheet of PAI-1. When the secondary peptide structure was assessed, the active serpin-derived peptides, S-1 and S-3 with RN or RNL, demonstrated the potential for helical sections (Expasy).

Peptide Expression and Purification.

Neuroserpin was expressed in BL21 (DE3) pLysS cells (Invitrogen, Carlsbad, Calif., USA) as previously described (Munuswamy-Ramanujam (2010) Thromb Haemost 103: 545-555). In brief, cells induced with 1 mM IPTG (Isopropyl β-D-1-thiogalactopyranoside) for 3 h were pelleted, re-suspended in elution buffer (20 mM Tris+20 mM Imidazole+150 mM NaCl) containing EDTA free complete protease inhibitors (Roche) and 2 mM 4-(2-Aminoethyl) benzenesulfonyl fluoride hydrochloride (AEBSF), and French pressed. Cell debris was pelleted at 15,000 rpm and supernatant loaded onto 500 µl of cobalt NTA slurry (Sigma-Aldrich, St. Louis, Mo., USA). The majority of the NSP was localized in inclusion bodies, but sufficient soluble active protein was expressed (39.5 µg/50 ml of culture).

Serp-1 was purified from the supernatant of recombinant Chinese hamster ovary (CHO) cell line as previously described (provided by Viron Therapeutics Inc., London, ON, Canada; Dai, et al. (2003) J Biol Chem 278: 18563-18572; and Tardif, et al. (2010) Circ Cardiovasc Interv 3: 543-548). Serp-1 purity was over 95% as determined by overloaded Coomassie-stained SDS-PAGE gels and reverse-phase HPLC.

Serpin peptide metabolite sequences were predicted by the PeptideCutter utility of Expasy program (the Expert Protein Analysis System) World Wide Web server (see, http://www.expasy.org) and synthesized by the University of Florida Peptide Centre. The physicochemical characteristics provided in FIG. 1 were calculated using PepDraw (Wimley lab, Tulane University, New Orleans La.).

Cell Cultures.

Human monocytic THP-1 cell line (TIB-202) and T-lymphocyte Jurkat cells (E6.1 clone, TIB-152) were procured from American Type Culture Collection, Rockville, Md., USA and cultured in RPMI medium supplemented with 10% Fetal Bovine Serum (Invitrogen Canada Inc., Burlington, ON, Canada), Penicillin (1 U/ml) and Streptomycin (1 mg/ml) (Invitrogen Canada Inc., Burlington, ON, Canada), with 2% L-Glutamine and 1% Sodium Pyruvate (Invitrogen Canada Inc., Burlington, ON, Canada) added for Jurkat cells. Cells were maintained at a confluence of $0.5-1.0 \times 10^6$ cells/mL (Viswanathan K, et al. (2009) B. J Leukoc Biol 85: 418-426; and Viswanathan K, et al. (2012) PLoS One 7: e44694).

Protease and Serpin Inhibitory Activity Assay.

Activity of purified NSP and Serp-1 was measured as inhibitory activity for uPA, using a chromogenic assay (Assaypro, St. Louis, Mo., USA) as previously described (for example, see, Dai E, et al. (2003) J Biol Chem 278: 18563-18572). Serp-1, NSP or individual peptides were mixed with enzyme solution at room temperature for one hour, per the manufacturers protocol (American Diagnostics). After incubation, 10 µl of chromogenic substrate was added. The 96-well plate was covered and placed in a wet box for overnight incubation at 37° C. After a 17 hr incubation, the plate was read at 405 nm by microplate reader (Bio-Tek Instruments). Reaction buffer (100 mM NaCl, 2 mM $CaCl_2$, 100 mM Tris-HCl, pH 7.5, Triton X-100, 0.005%) was used for dilutions of proteases, Serp-1, NSP, or serpin peptides and chromogenic substrate. Residual protease activity was calculated with comparison to control samples without active serpin or peptides.

Serpin inhibition activity of peptides was also assessed using assays for uPA, tPA, plamin, PAI-1 and anti-thrombin III (ATIII). SensoLyte® fluorimetric assay kits were purchased from Anaspec (Fremont, Calif.) for tPA (AS-72160), plasmin (AS-72124) and thrombin (AS-72130) and assays were conducted per the manufacturer's specifications. Peptide inhibition of ATIII (ThermoFisher Scientific, Grand Island, N.Y.) was measured as a reduction in its thrombin activity. uPA (Sigma, U0633) activity towards pefachrome uPA (Enzyme Research Laboratories, South Bend, Ind., P082-33) was used for assaying peptide inhibition. Modulation of the inhibitory activity of PAI-1 (Peprotech, Rock Hill, N.J., 140-04) towards uPA by peptides was also assayed.

All assays were performed in triplicate. On chromogenic assay, Serp-1 and NSP inhibited uPA. None of the peptides, however, reduced uPA protease activity (FIG. 2).

Example 2: Select Serpin-Derived Peptides Modify Spleen Cell Responses

Effects on early inflammatory cell invasion were assessed in a mouse ascites model. To investigate whether peptides would also actively modify cell invasion for selected cell types, cellular migration responses were examined after chemokine injection into the peritoneum (i.p. injection). Prior work demonstrated that Serp-1 and NSP modify Th1 and Th2 responses. Intraperitoneal (i.p.) chemokine (MCP-1) injection was used to induce mononuclear cell migration into the peritoneal cavity of mice. None of the serpin-derived peptides altered cell migration into ascites fluid at 18 h (data not shown). However, when examining these same mice for systemic effects on spleen cell populations, cells isolated from spleens in mice after MCP-1 injection demonstrated altered cell responses with S-1 and S-6 treatment. S-1 and S-6 significantly reduced CD11b (FIG. 3B; P<0.05), while S-3 and S-5 did not. Although S-3 showed a trend toward reduced CD11b percentage, this trend did not achieve significance. Of the serpin-derived peptides, S-6 significantly altered CD3+CD4+ T cell counts (P<0.05; FIG. 3A). Th1 (CD4+IFNγ+, FIG. 3C), CD4+Th2 (IL4+, FIG. 3D), Treg (FoxP3, FIG. 3E), and Th17 (IL17a+, FIG. 3F) were not altered with peptide treatment.

Mouse Peritoneal Cell Migration Assay.

Mice were injected with monocyte chemoattractant protein-1 (MCP-1) and treated with Serp-1, NSP or individual serpin-derived peptides (i.v.). Three mice were tested per serpin or serpin-derived peptide treatment. Cell counts were obtained by flow cytometry. Cells isolated from mouse ascites were stained with antibodies to surface or intracellular antigens and incubated for 30 min at room temperature (Viswanathan et al., (2012) PLoS One 7:e44694). Labeled cells were washed and re-suspended with 150 µl of PBS and assessed by flow cytometry. For staining of intracellular antigens, cell pellets in 500 µl were incubated with fixation/permeabilization buffer (eBioscience, San Diego, Calif., USA), incubated in the dark for 45 min, treated with permeabilization buffer (eBioscience San Diego, Calif., USA), and incubated with intracellular antibody mix, with further incubation for 30 min at 4° C. All antibodies were purchased from eBiosciences and Biolegend (San Diego, Calif., USA). Flow cytometry was performed with a CyAn ADP Analyzer (Dako, Ft Collins, Colo., USA) (Chen et al., (2013) Antimicrob Agents Chemother 57:4114-4127; Munuswamy-Ramanujam et al., (2010) Thromb Haemost 1103:545-555; and Viswanathan et al., (2012) PLoS One 7:e44694). Data analysis was done using Gatelogic software (eBioscience).

Example 3: Serpin-Derived Peptides Modify Cell Activation Measured by Membrane Fluidity Cellular membrane fluidity is measured by pyrene dimer formation in the lipid bilayer and is used as a non-specific measure of cell activation (Zalai C V, et al. (2001) J Am Coll Cardiol 38: 1340-1347). Increases in THP-1 human monocyte membrane fluidity, after PMA activation, correlate with changes in cell activation, adhesion and motility. DPP (pyrene) labeled cells treated with Serp-1 or NSP demonstrated significant changes in the eximer (dimer) to monomer fluorescence emission intensity ($I_{Ex}/I_{Mon}$) ratios (FIG. 4) in PMA activated human THP-1 cells in culture. For instance, membrane fluidity assays measured as Iex/Imon fluorescence of BPP labeled THP-1 monocytes demonstrated increased Iex/Imon ratios with PMA activation. Serpin-derived peptide treatments paralleled in vivo activity with the one exception being the S-4 peptide. The S-6 peptide, which caused excess thrombosis, displayed inhibitory activity for cells. All serpin-derived peptides were tested at three doses 500, 1000 and 1500 ng/ml. Serp-1 peptides, S-1 and S-3, and NSP peptides, S-4, S-6 and S-8, significantly reduced PMA mediated increases in the $I_{Ex}/I_{Mon}$ ratio, a measure for cell activation, with varying concentration dependent activity.

S-6 reduced $I_{Ex}/I_{Mon}$ ratios at all doses (P≤0.007), while S-4 was active at the two higher concentrations (P≤0.015). S-1, S-3, S-7, and S-8 were inhibitory at the highest concentration, 1500 ng (S-1–P<0.027; S-3–P<0.007; S7–P<0.03, S-8–p<0.017). S-2 and S-5 did not significantly alter $I_{Ex}/I_{Mon}$ (S-2–P=0.07; S-5–P=0.057). Thus, analysis of membrane fluidity detected concentration dependent variations in cell responses to serpin-derived peptide treatments with the greatest sensitivity to treatment seen with S-6 followed by S-3 and S-4. S-1, S-7 and S-8 had less activity in this assay requiring higher concentrations. S-2 and S-5 were inactive.

Data from this cell activation assay suggests that serpin-derived peptides, S-2 and S-5, which lack anti-atherogenic activity in vivo after allograft transplant, did not modify THP-1 cell activity. The other serpin-derived peptides that displayed significant activity in the in vivo allograft transplant model, both protective and anti-atherogenic (S-1, S-3, S-7, S-8) or pro-thrombotic (S-6) also modified cell activation in the membrane fluidity assay. The capacity to produce beneficial inhibition of vascular inflammation and plaque growth was inversely proportional to the capacity to modify THP-1 human monocyte activation with S-6 having greatest activity at lower doses than S-1, S-3 and S-7. The lack of activity for S-2 and S-5 did correspond to a lack of inhibitory activity for plaque growth. S-4 was an exception having effects on membrane fluidity, but no efficacy in the allograft model.

In summary, the effects on monocyte activation were varied, but some correlation between inhibition of vascular plaque growth after aortic engrafting for serpin-derived peptides and inhibition of monocyte activation in vivo was demonstrated. S-1, S-3, S-6, S-7, and S-8 reduced membrane fluidity while S-2 and S-5 were inactive (FIG. 4). S-4 was an outlier, demonstrating reduced membrane fluidity and marked variation in plaque growth from very small to very large plaque. This variability led to a non-significant change in plaque growth with S-4 treatment. In the mouse ascites assay, S-1, S-3 and S-6 altered splenocyte CD3+ CD4 and Cd11b responses to varying extents (FIG. 6). These data support systemic immune modulatory actions for selected serpin-derived peptides. In the model used here, an inflammatory response was induced by injection of a chemokine into the peritoneal cavity followed by intravenous administration of the serpin-derived peptides. While no consistent effect was detected on mouse peritoneal mononuclear cell migration into the peritoneal cavity, a systemic effect on spleen cell population subsets was detected. Nonspecific changes in CD3+CD4+ were detected for S-6 alone and on CD11b for S-1 and S-6 with a trend for S-3. None of the serpin-derived peptides produced a significant change in T helper (Th) subsets, Th1, Th2, Th17 or Treg. These findings may be due to the small effect of intraperitoneal injection on systemic inflammation, as serpin activity has been previously shown to often be more pronounced in animal models with marked increases in inflammation, e.g. angioplasty, stent implant of allograft transplants.

Membrane Fluidity Cell Activation Studies.

One million >95% viable THP-1, Jurkat T, or 5×10⁵ HUVEC cells were labeled with BPP (0.8 µM) for studying core membrane fluidity, three hours prior to cell activation as previously described (Viswanathan K, et al. (2009) B. J Leukoc Biol 85: 418-426; Viswanathan K, et al. (2006) Thromb Haemost 95: 499-510; Zalai C V, et al. (2001) J Am Coll Cardiol 38: 1340-1347; Viswanathan K, et al. (2012) PLoS One 7: e44694; and Christov A, et al. (2001) Lasers Surg Med 28: 414-426). Cells were activated with PMA (1 µg/mL) for one hour, washed, resuspended in growth medium and treated with either Serp-1 (500 ng/mL), NSP (500 ng/mL), or individual serpin-derived peptides at (500, 1000 or 1500 ng/mL) for one hour. All assays were performed in triplicate. At the end of one hour, cells were washed to remove excess fluorescent probe and monomer, excimer fluorescence emission intensities were measured at 390 nm and 485 nm, respectively, during excitation at 320 nm using a fluorescent dual wavelength reader (Fluoroskan, Thermolab systems, Oy, USA). The ratio of excimer fluorescence to monomer fluorescence gives the measure of membrane fluidity.

Example 4: Serpin-Derived Peptide Mediated Changes in Gene Expression

Shared effects of Serp-1 and S-1, one of the active Serp-1 RCL peptide inhibitors for plaque growth, on transcription of representative genes in signaling pathways were studied in human Jurkat T cell (FIG. 5A and FIG. 5B) and THP-1 monocytes (FIGS. 5C-7F). The inactive S-5 peptide, which did not reduce plaque, was similarly tested in parallel for effects on gene expression in the same cell lines. Serp-1 and the Serp-1 peptides (serpin-derived peptides) S-1 and S-5 were compared to saline treated controls. Genes with two-fold change in expression with P-value less than 0.05 by Student's t-test were considered significant.

Figures 5A, 5B, 5C, 5D, 5E, 5F:
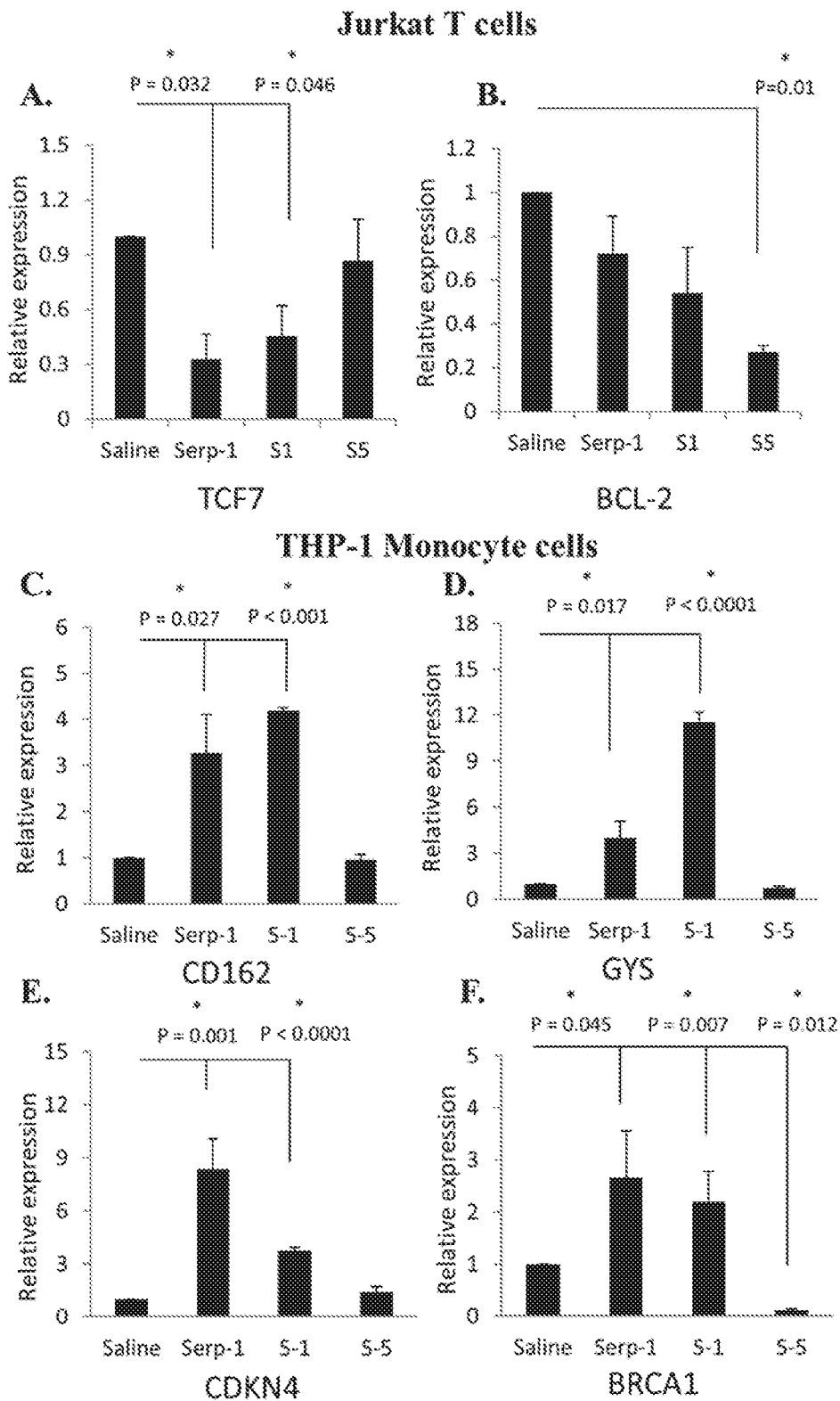

Treatment of Jurkat cells did not effect a 2-fold change in any of the genes tested but both Serp-1 and S-1 inhibited transcription factor 7 (TCF7) (P<0.046), whereas S-5 treatment did not (FIG. 5A). Other genes were significantly reduced by S-5 peptide in T cells but were not modified by Serp-1 or S-1. Of these genes, S-5 reduced BCL-2 (FIG. 5B) and also chemokine CCL 20 (P<0.03), CCND-1 (P<0.01), interleukin-8 (IL-8; P<0.009), and matrix metalloproteinase 7 MMP7 (P<0.004) (data not shown), whereas S-1 and Serp-1 had no effect, suggesting that reductions in the expression of these genes in T cells may provide no protection in arterial disease.

In THP-1 cells, both Serp-1 and S-1 increased expression for four genes by at least 2-fold. Selectin P ligand (CD162, P<0.027), glycogen synthase (GYS, P<0.017) and cyclin-dependent kinase inhibitor 1B (CDKN1; p27, P<0.001) were induced by Serp-1 and S-1 peptide treatment while S-5 peptide treatment did not increase expression (FIGS. 5C-5E). Both Serp-1 and S-1 induced the expression of breast cancer 1 gene (BRCA1, P<0.045) in THP-1 cells while S-5 inhibited BRCA1 significantly (P<0.012) (FIG. 5F). BRCA1 has demonstrated protective activity in mice against endothelial cell apoptosis, dysfunction and inflammation. GYS, which is associated with glycogen storage disease, and CDKN1 do not have reported direct effects on atherogenesis nor arterial inflammation to date. These studies suggest that the serpin Serp-1 and the Serp-1 RCL peptide S-1 share the capacity to significantly alter gene expression in human monocytes and Jurkat T cells and, more specifically, inflammatory responses such as inflammatory monocyte and T cell differentiation in atherogenesis. Changes in gene expression for Serp-1 and S-5 differed from the RCL peptide S-5 potentially representing differing pathways modified by the serpins and serpin-derived peptides that reduce plaque growth and those that do not.

The differences in the expression of signaling genes between Serp-1 and S-1 treatments on one hand and S-5 treatment on the other hand, offer potential mechanisms of action by which serpin-derived peptides such as S-1 can exert anti-atherogenic actions (FIG. 5). BRCA1 has recently been shown to be an essential regulator of heart function (Shukla P C, et al. (2011) Nat Commun 2: 593) and is anti-atherogenic (Singh K K, et al. (2013) J Thorac Cardiovasc Surg 146: 949-960 e944). TCF7 is involved in the differentiation of thymocytes and is indispensable for their development (Ma J, et al. (2012) J Neuroimmune Pharmacol 7: 750-76). The modulation of these genes may be linked to the protective effects of Serp-1 and S-1.

RT-PCR Gene Expression Analyses.

To further examine potential mechanisms of inhibitory activity for individual serpin peptides, THP-1 monocyte and Jurkat T cells in culture were treated with individual serpins or serpin-derived peptides with proven inhibitory activity for plaque growth in vivo (Viswanathan K, et al. (2009) B. J Leukoc Biol 85: 418-426; Viswanathan K, et al. (2006) Thromb Haemost 95: 499-510; Chen H, et al. (2013) Antimicrob Agents Chemother 57: 4114-4127; and Viswanathan K, et al. (2012) PLoS One 7: e44694). RT-PCR signaling pathway gene arrays (Sigma-Aldrich, St. Louis, Mo., USA) were analyzed in triplicate per cell type using predicted peptide or serpin treatment.

Statistics. For the above Examples, changes in plaque area, intimal/medial thickness ratios, inflammatory cell invasion, as well as membrane fluidity and cellular adhesion were assessed by analysis of variance (ANOVA) and Student's T-test. Mean values were calculated for plaque area and intimal/medial thickness ratios for each mouse and used for subsequent statistical analysis. For PCR arrays, a two-tailed Student's t-test was conducted between saline controls and the treatments. For the viral infection studies, Kaplan Meier survival analyses were performed. P<0.05 was considered significant.

Example 5: Serpin-Derived Peptide S-7 Improves Survival in Lethal MHV68 Infected Mouse Model Serpin-derived peptides, S-2 and S-7, were examined for their ability to improve outcome in a mouse model of lethal viral sepsis (gammaherpesvirus 68 (MHV68) infection in gamma interferon receptor (IFN-γR) knockout mice). MHV68 is a standard model for human inflammatory vasculitis and lethal herpes virus infections.

Treatment with S-7, not S-2, significantly prolonged survival in gamma interferon receptor-deficient mice (FIGS. 6 and 7). Saline and S-2 treatment in MHV68-infected IFN-γR knockout mice did not improve survival, with a trend toward increased mortality.

MHV68 Virus Passage and Preparation.

MHV68 was a gift from the Virgin lab (Dal Canto et al. (2011) J. Clin. Invest. 107:R15-R22; Krug et al. (2010) Am. J. Pathol. 177:608-621). Viral MHV68 stocks were generated in 3T12 cells (ATCC, Manassas, Va.). 3T12 cells were cultured in D-MEM+10% FCS+10 mM HEPES+2 mM L-Glutamine+1% Pen/Strep. At 50% confluency, cells were infected with MOI of 0.1. Seven days post infection, cells underwent freeze thaw and lysate was transferred to Nalgene Oak Ridge PPCO tubes and centrifuged (15 min at 4300×g). Cleared supernatant was centrifuged for 2 hrs at 12,000×g. The pellet was rinsed with PBS, and re-suspended in media, vortexed, and stored at −80° C. in 250 μl aliquots. Virus was titered in duplicate.

Experimental Animal Protocols.

Pure Interferon gamma receptor knock out (IFNγR$^{-/-}$) mice (B6.129S7-Ifngrl$^{tm1Agt}$/J), 5-7 weeks of age, were purchased from JaxLabs (Sacramento, Calif., USA) and bred under specific pathogen free condition. Littermate controls were used for all studies.

MHV68 Infection.

Ninety (6-10 mice per group) IFNγR$^{-/-}$ mice were infected by intraperitoneal (i.p.) injection of 12.5×10$^6$ PFU or 6×10$^6$ PFU MHV68 given in 0.1 ml DMEM (Dal Canto et al. (2011) J. Clin. Invest. 107:R15-R22). Mice were treated with either saline to serve as a control (100 μl) or individual serpin-derived peptides (S-1, S-3, S-5, S-7 or S-2, S-4, S-6 or S-8; 100 μg/kg/100 μl) which were given at the time of infection and then daily by intraperitoneal (i.p.) injection for a total of 30 days starting on the day of MHV68 infection or until the animals displayed severe findings of sepsis necessitating sacrifice for humane reasons. Serpin-derived peptides (S-2 and S-7) were administered as treatment for 30 days (n=6-10 mice per treatment group). Mice were followed up for a maximum of 150 days. Mice were carefully monitored by the veterinary animal care staff to minimize potential suffering. Euthanasia was performed as previously described.

In Vitro MHV68 Replication Assay.

NIH 3T12 murine fibroblasts were infected in vitro with wild-type MHV68 at MOI 0.05 in the absence or presence of 500 ng/mL of Serp-1. At 96 hours post-infection, cells and supernatant fluid was harvested, and viral titers determined by plaque assay. Plaque assays were performed on NIH 3T12 cells. Briefly, 10-fold serial dilutions of samples were prepared in serum-free DMEM, then infections were performed in 400 μL at 37° C. for 1 hour. Cells were then overlaid with a 1:1 mixture of methylcellulose (Sigma) and MEM supplemented with 10% fetal calf serum and antibiotics. At 7 days post-infection, plaques were visualized by neutral red staining and counted.

Histological and Morphometric Analysis.

At follow up, mice were euthanized and organ tissue harvested as well as blood samples. All specimens from MHV68 infected mice, with or without serpin treatment, were cut into 2 equal lengths (aorta; 3 to 5 mm and other organs; 0.5 cm) and then cut into halves, one for histology and one for mRNA and protein analysis. Sections from Ebola mouse tissues were fixed in BSL4 facility following approved standard operating protocols and then used for histology. For histology, sections were fixed in neutral buffered formalin (NBF), embedded in paraffin, and cut into 4 μm thick cross sections and stained with haematoxylin and eosin, as described (Chen et al. (2011) Methods Enzymol. 499:301-329; Lucas et al. (2009) Adv. Exp. Med. Biol. 666:132-156). Cellular invasion and tissue hemorrhage and necrosis were measured using an Olympus DP71 camera attached to an BX51 microscope (Olympus America Inc., Center Valley, Pa.) and quantified using Image Pro 6.0 (MediaCybernetics Inc., Bethesda, Md.) (14-21).

Statistical Analysis.

Statistical analysis was performed using Statview V5.01 (Cary, N.C., USA). Survival was assessed by Kaplan Meier analysis. Mice requiring early euthanasia prior to the designated follow up time were included in survival analyses. Mean cell counts or areas of tissue hemorrhage or necrosis were calculated from three sections for each specimen isolated from each mouse. Mean values were used for subsequent statistical analyses. Multiple group comparisons were performed using analysis of variance (ANOVA) with Fishers PLSD (Protected Least Significant Difference) and unpaired two-tailed Student's t-test for subgroup analysis; P<0.05 was considered significant.

Example 6: Selected Serpin-Derived RCL Peptides Reduce Plaque Growth

To assess potential anti-inflammatory actions of individual serpin-derived peptides, peptide treatment was tested in mice after aortic allograft transplant at 4 weeks. In engrafted aorta, serpin-derived peptides containing R or RN, specifically S-1, S-3, S-7 and S-8, significantly reduced plaque growth (FIGS. 9 and 10). Histological cross sections demonstrate altered plaque growth when comparing serpin-derived peptides (n=93 mice, 15 μg dose immediately after transplant). Conversely, the S-6 peptide lacking R or RN with excess negative charge (−4), induced early thrombosis and mortality and RN containing peptide S-4 was inactive. Histological analysis showed increased plaque in cross sections of engrafted aortic arteries with saline treatment (FIGS. 9A and 9B). Analysis of histologic cross sections demonstrated significantly reduced inflammatory plaque area after treatment by either the Serp-1 derived RCL peptides S-1 (FIGS. 9D, 9G, 9H and 10A and 10C), S-3 (FIG. 9G, 9H; P<0.045), and S-7 (FIG. 9E, 9F, 9G, 9H; P<0.036), or NSP peptide S-8 (FIG. 3G, 3H; P<0.034) given at 15 μg doses. S-5 (FIG. 9C, 9G, 9H and FIG. 10B) and S-2, S-4, and S-6 (FIG. 9G, 9H) did not significantly alter plaque growth. Of interest, S-6 treatment at the same 15 μg dose as for other peptides produced universal early thrombosis at the site of aortic allograft transplant with 100% mortality (Table 1). When S-6 was given at tenfold lower doses (1.5 μg) than other serpin-derived peptides given at 15 μg doses, there was no effect on plaque growth (FIG. 9G, 9H).

TABLE 1

Mouse Aortic Allograft Transplant Surgeries.

| Treatment | Dose/mouse | Number Mice Transplanted (Donor B6*/PAI-$1^{-/-}$) | Number Survived 4 weeks | Adverse Events |
|---|---|---|---|---|
| Saline | 0 | 11 (6 B6/5 PAI-$1^{-/-}$) | 10 | 1 thrombosis |
| NSP | 15 μg | 5 (0 B6/5 PAI-$1^{-/-}$) | 4 | 1 thrombosis |
| NSP-PP RCL mutant | 15 μg | 5 (0 B6/5 PAI-$1^{-/-}$) | 4 | 1 hematoma |
| S-1 | 1.5 μg | 6 (0 B6/6 PAI-$1^{-/-}$) | 6 | 0 |
| S-1 | 15 μg | 10 (5 B6/5 PAI-$1^{-/-}$) | 8 | 1 thrombosis, 1 fighting injury |
| S-1 | 150 μg | 4 (0 B6/4 PAI-$1^{-/-}$) | 4 | 0 |
| S-2 | 15 μg | 5 (5 B6/0 PAI-$1^{-/-}$) | 4 | 1 thrombosis |
| S-3 | 15 μg | 6 (6 B6/0 PAI-$1^{-/-}$) | 6 | 0 |
| S-4 | 15 μg | 5 (5 B6/0 PAI-$1^{-/-}$) | 5 | 0 |
| S-5 | 1.5 μg | 4 (0 B6/4 PAI-$1^{-/-}$) | 4 | 0 |
| S-5 | 15 μg | 6 (0 B6/6 PAI-$1^{-/-}$) | 6 | 0 |
| S-5 | 150 μg | 4 (4 B6/0 PAI-$1^{-/-}$) | 4 | 0 |
| S-6 | 1.5 μg | 6 (6 B6/0 PAI-$1^{-/-}$) | 6 | 1 thrombosis |
| S-6 | 15 μg | 6 (0 B6/6 PAI-$1^{-/-}$) | 0 | 6 thromboses |
| S-7 | 15 μg | 5 (0 B6/5 PAI-$1^{-/-}$) | 5 | 0 |
| S-8 | 15 μg | 5 (0 B6/5 PAI-$1^{-/-}$) | 5 | 0 |
| Total number mice | | 93 (37B6/56PAI-$1^{-/-}$) | 81 | 12 |

*C57BL/6 is abbreviated as B6 here

Plasminogen activator inhibitor-1 (PAI-1) is one of the main thrombolytic (clot dissolving) pathway regulators functioning to inhibit tPA, uPA, and also the clotting factor thrombin in the presence of heparin. PAI-1 has been variably reported to act as an anti-atherosclerosis agent and a pro-atherogenic agent in differing animal models of vascular disease. It has been previously shown that Serp-1 treatment reduced plaque growth and inflammation in PAI-1−/− aortic allograft implants. In this study, a trend toward increased plaque growth in engrafted PAI-1−/− aortas was observed when compared to C57BL/6 WT aortic allograft transplants after implant in Balb/C mice; however, this increased plaque did not reach significance (P=0.106). S-1 peptide treatment was compared for PAI-1−/− and for C57BL/6 donor allograft (Table 1, FIG. 10C). When all data was combined for PAI-1−/− and C57BL/6 WT donor allografts, S-1 significantly inhibited plaque growth (FIGS. 9G and 9H; P≤0.009). When data was separated for S-1 treatment after PAI-1−/− and C57BL/6 WT donor allograft transplant, S-1 inhibition was greatest in PAI-1 deficient aortic allografts with significant reductions in plaque area (FIG. 10C; P<0.001).

S-1 and S-5 peptides were assessed for dose dependent reductions in plaque. S-1 significantly reduced plaque area at both doses (FIG. 10A), while S-5 displayed some inhibition of plaque growth, but only at a 10-fold higher dose infusion (FIG. 10B). S-1 had equivalent activity at the doses tested (FIGS. 10A and 10C) and S-5, although showing some improved efficacy at the higher dose, did not reach significance (FIG. 10B). S-3 was active as was S-1 in reducing plaque growth, with similar efficacy; however, S-3 was limited to testing in C57BL/6 (WT) aortic allograft implants. Invasion into intima was reduced by all the peptides derived from Serp-1 and S-4 and S-8 (peptides derived from NSP). Adventitial cell counts were reduced with S-3 and S-8 significantly. (P<0.05 considered significant). The majority of effective serpin-derived peptides were tested in PAI-1−/− donor allograft transplants, which might suggest that serpin-derived peptide efficacy was more dependent on the donor allograft implanted. S-6 was, however, tested at the lethal 15 µg dose in PAI-1−/− allografts and an inactive NSP-PP with a mutated RCL P1-P1′ site was similarly tested in PAI-1−/− allografts and neither reduced plaque growth (FIGS. 9 and 10). The increased thrombosis in the S-6 15 µm treated allograft transplants as noted above was detected in PAI-1−/− allograft implants. These results suggest that PAI-1−/− allografts may have increased local thrombolysis due to the lack of PAI-1 mediated blockade of tPA and uPA. The capacity of S-6 to markedly increase thrombosis causing 100% mortality when infused at 15 µg doses further suggests an extension of normal PAI-1 regulatory function as a thrombolysis inhibitor, causing clot formation (thrombosis).

Mouse Aortic Transplant Models.

Ninety three mice had aortic allograft transplantation; 56 had PAI-1−/− (C57BL/6 background) donor to BALB/c (PAI-1+/+) recipient; and 37 had C57BL/6 wild type (PAI-1+/+) to BALB/c (PAI-1+/+) recipient. PAI-1 deficient mice (PAI-1−/−) have been variably reported to have increased and, alternatively, decreased plaque after vascular injury. Due to the large number of surgeries required, both the PAI-1−/− and the WT mouse implants were utilized. The PAI-1−/− mice also allowed analysis of serpin response in a mouse transplant lacking a key thrombolysis regulating serpin, PAI-1. A 0.3 cm aortic segment isolated from the donor mouse was transplanted into the infra-renal aorta of recipient mice for aortic allograft studies (Table 1). The aortic transplant was anastomosed end-to-end using Sharpoint 11/0 nylon sutures (Surgical Specialties Corporation, Reiding, Mass., USA) under general anesthetic (6.5 mg/100 g body weight Somnotrol, MTC Pharmaceuticals, Cambridge, ON, Canada) given by intramuscular (i.m.) injection. WT C57BL/6 mice were purchased directly from Jackson Laboratories (Bar Harbor, Me., U.S.A.) and PAI-1−/− mice were bred in-house using mice supplied by Jackson Laboratories prior to surgery. Mice were followed for 4 weeks after transplant. A single infusion of either individual proteins (Serp-1 or NSP) or individual serpin-derived peptides (15 µg/mouse; 0.75 µg/gm body weight in 0.2 ml) was administered. Once reduced plaque was detected at 15 µg doses, a dose titration curve was completed for two of the individual serpin-derived peptides that displayed apparent anti-inflammatory and transplant vasculopathy inhibitory activity (4-10 mice per treatment; 1.5, 15 and 150 µg/mouse). Serpins or serpin-derived peptides were infused by intravenous (i.v.) tail vein injection immediately after transplant surgery, once aortic pulsation was again visible.

At 4 weeks after aortic transplant, mice were euthanized with 0.05 ml euthanyl (Bimeda—MTC Animal Health Ltd., Cambridge, ON, Canada) by i.m. injection.

Histological and Morphometric Analysis.

Donor aortic transplant implants and adjacent recipient aorta (0.5-0.6 cm long) were cut into two 0.25-0.3 cm pieces, fixed, paraffin embedded, and cut into 5 µm sections (two per aortic section, providing 4 sections for analysis of each transplanted mouse aorta) and stained with Haematoxylin and eosin for morphometric analysis. Areas of plaque, lumen and internal elastic lamina were measured by means of the Olympus application program using a Sony Power HAD3CCD color video camera attached to the microscope and calibrated to the microscope objective. The mean total cross sectional area of the intima, using sections with the largest detectable plaque area, was calculated for each aortic specimen. Numbers of invading mononuclear cells were counted per high powered field area at three sites in the intimal, medial and adventitial layers and the mean count for each arterial layer and specimen calculated.

Example 7: In Silico Modeling of Potential for Protease and Serpin Inhibitory Functions The docking of the S-2 peptide into ATIII did not show any significant interactions between the serpin-derived peptide and serpin, with a few potential hydrogen bonds observed; with a calculated ligation solvation energy of −27 kJ/mol (data not shown). Many more interactions were observed in the ATIII/S-7 complex. This longer peptide made significant contacts with neighboring side chains in ATIII (estimated ~5-fold more than in the ATIII/S-2 complex). The majority of the interactions at the interface were hydrogen bonds, with a calculated ligation solvation energy of −24.7 kJ/mol.

The PAI-1/S2 complex also shows little potential for hydrogen bonds, even fewer than in the ATIII/S-2 complex. This may be a consequence of the compact nature of PAI-1 (β-barrel, compared to ATIII. The S2 peptide wedged between a narrow opening between two parallel β-strands. This most likely explains the lower ligation energy of −17 kJ/mol. In addition, unlike ATIII, which consists of 5 β-strands, PAI-1 consists of 4 β-strands. The PAI-1/S-7 complex displayed the highest calculated ligation solvation energy among the four models of −38 kJ/mol. This observation was likely due to the ability of the S-7 peptide to make additional interactions with a loop region distance from the β-sheet. In contrast, the shorter bulkier S-2 peptide was unable to make these interactions.

In the case of both ATIII and PAI-1, it appears that both serpins favor interactions with the longer S-7 peptide due to its ability to form interactions in the neighboring side chains of amino acids within the β-sheet.

In Silico Modeling of Potential Protease and Serpin Inhibitory Functions.

The RCL insertions were modeled into the β-sheet of a neighboring serpin. Two serpin-derived peptide (S-1 and S-7) complexes with serpin ATIII and PAI-1 (PDB IDs: 2B4X and 1DB2, respectively) were generated.

The central antiparallel β-strand of the β-sheet of both full-length serpin was deleted and the S-2 and S-7 peptides were manually rigid-body docked into the vacated space. Steric clashes between the serpin-derived peptide and serpin were corrected by selection of alternate rotamers in the serpin and/or serpin-derived peptide. The following complexes were built: ATIII/S-2, ATIII/S7, PAI-1/S-2 and PAI-1/S7. The resulting complex coordinates were analyzed with PDBePISA (Barata et al. (2011) PLoS Comput Biol 7:e1002095; Anbanandam et al. (2008) J Mol Biol 384:219-227; and Raguine et al. (2013) Chem Biol Drug Des 81:167-174) to measure the solvation energy upon ligation and to account for any favorable interactions between the peptide and serpin.

Example 8: Analysis of Inflammatory Cell Invasion

Inflammatory mononuclear cell infiltrates into the arterial wall were measured in the intimal layer. Increased cell invasion was seen at 28 days follow up in aortic allograft sections. Reduced counts for invading MC for all the serpin-derived peptides tested were observed except S-4 and S6, demonstrating some correlation with plaque reductions seen for S-1, S-3, S-7 and S-8, but not correlating with S-2 and S-5 treatment, where no significant reduction in plaque was detected (FIG. 10D). For the adventitial layer, S3 and S8 significantly reduced mononuclear cell counts (FIG. 10E), while S-1 and S-7 did not. Thus, a consistent association was not detected between serpin-derived peptide treatments, plaque inhibition and inflammatory cell invasion into the arterial wall. This may be due to the fact that these sections were taken at late follow up times after aortic grafting and treatment. Thus, effects on early inflammatory cell invasion were assessed in a mouse ascites model as described in Example 2.

Example 9: Serpin-Derived Peptide S-7 Improves Survival in Lethal MHV68 Infections in IFNγR$^{-/-}$ Mice To further determine whether serpin-derived peptides with anti-inflammatory activity in the aortic transplant model had beneficial functions in other in vivo models, serpin-derived peptides were assessed in a lethal MHV68 infection in IFNγR deficient mice, a model for virus-induced vasculitis. Infected mice were treated with either S-1, S-2, S-3, S-7, an inverted sequence or S-8. S-7 was active with a significant improvement in survival (FIG. 11A). As for the aortic transplants, S-2 showed no activity (FIG. 11B). Differing from the aortic transplant model, no other serpin-derived peptides examined improved survival in this model (data not shown). S-7 was tested in two independent studies with two differing MHV68 stocks. The S-7 inverted peptide did not improve survival demonstrating that the peptide sequence was important to this activity.

MHV68 Infection in IFNγR$^{-/-}$ Mice.

Viral MHV68 stocks were generated in NIH 3T12 fibroblasts (ATCC, Manassas, Va.). Cells were cultured in D-MEM+10% FCS+10 mM HEPES+2 mM L-Glutamine+ 1% Pen/Strep. At 50% confluency, cells were infected with MOI of 0.1. Seven days post-infection, cells underwent freeze thaw and lysate was transferred to Nalgene Oak Ridge PPCO tubes and centrifuged (15 min at 4300×g). Cleared supernatant was centrifuged for 2 h at 12,000 g. The pellet was rinsed with PBS, and re-suspended in media, vortexed, and stored at −80° C. in 250 µl aliquots. Virus was titered in duplicate.

Interferon gamma receptor knock out (IFNγR$^{-/-}$) mice (B6.129S7-Ifngrl$^{tm1Agt}$/J) and wild type mice (BALB/c), 5-7 weeks of age, were purchased from Jackson Laboratories (Bar Harbor, Me., USA) and bred under specific pathogen free condition. Littermate controls were used for all studies. 90 IFNγR$^{-/-}$ mice (6-10 mice per group) were infected by intraperitoneal (i.p.) injection of 12.5×106 PFU MHV68 given in 0.1 ml DMEM. Mice were treated with either saline control (100 µl), or individual serpin-derived peptides (S-1, S-2, S-3, S-7, S-8 or the inverted sequence, S-7) at 100 µg/kg/100 µl) given at the time of infection, and then daily by intraperitoneal (i.p.) injection for a total of 10 days starting on the day of MHV68 infection. Mice were followed up for a maximum of 150 days.

What is claimed is:

1. A recombinant polypeptide that binds to and inhibits activity of one or more serine protease enzymes, wherein the polypeptide consists of the amino acid sequence:

(S1)
                        (SEQ ID NO: 1)
IPRNAL;

(S3)
                        (SEQ ID NO: 3)
RNAL;

(S-6; SEQ ID NO: 6)
EVNEEGSEAAAVSGM;

(S7)
                        (SEQ ID NO: 7)
GTTASSDTAITLIPR.

2. A pharmaceutical composition comprising the recombinant polypeptide of claim 1.

3. A method of treating a patient who has or is at risk for an hemorrhagic viral infection, the method comprising administering to the patient a therapeutically effective amount of the recombinant polypeptide of claim 1.

4. The method of claim 3, wherein the recombinant polypeptide is administered by one or more of the following routes of administration: subcutaneous, intravenous, or intramuscular.

5. The method of claim 3, wherein the hemorrhagic viral infection is caused by exposure to a filovirus, optionally wherein the filovirus is Ebola or Marburg.

6. A method of treating a patient who has lethal viral, bacterial or fungal sepsis, the method comprising administering to the patient a therapeutically effective amount of a recombinant polypeptide comprising between 6 and 21 amino acid residues that binds to and inhibits activity of one or more serine protease enzymes, wherein the polypeptide comprises three contiguous residues of SEQ ID NO: 1.

7. A recombinant polypeptide comprising no more than 25 amino acid residues that binds to and inhibits activity of one or more serine protease enzymes, wherein the polypeptide comprises SEQ ID NO: 6.

8. The recombinant polypeptide of claim 7, wherein the polypeptide consists of the amino acid sequence: EVNEEG-SEAAAVSGM (S-6; SEQ ID NO: 6).

9. A method of treating a patient who has or is at risk for an hemorrhagic viral infection, the method comprising administering to the patient a therapeutically effective amount of the recombinant polypeptide of claim 7.

10. A recombinant polypeptide comprising no more than 25 amino acid residues that binds to and inhibits activity of one or more serine protease enzymes, wherein the polypeptide comprises at least 15 contiguous amino acid residues of SEQ ID NO: 8.

11. The recombinant polypeptide of claim 10, wherein the polypeptide consists of the amino acid sequence: MAV-LYPQVIVDHPFFFLIRNR (SEQ ID NO:8) (S8).

12. A method of treating a patient who has or is at risk for an hemorrhagic viral infection, the method comprising administering to the patient a therapeutically effective amount of the recombinant polypeptide of claim 10.

* * * * *

UNITED STATES PATENT AND TRADEMARK OFFICE
CERTIFICATE OF CORRECTION

Page 1 of 1

PATENT NO. : 10,550,172 B2
APPLICATION NO. : 15/559867
DATED : February 4, 2020
INVENTOR(S) : Alexandra Rose Lucas It is certified that error appears in the above-identified patent and that said Letters Patent is hereby corrected as shown below:

In the Claims

In Claim 1, Column 31, beginning at Line 29, the text:
"(S1)                                                               (SEQ ID NO: 1)
IPRNAL;

(S3)                                                                (SEQ ID NO: 3)
RNAL;

(S-6; SEQ ID NO: 6)
EVNEEGSEAAAVSGM;

(S7)                                                                (SEQ ID NO: 7)
GTTASSDTAITLIPR."

Should read:
--(S1)                                                              (SEQ ID NO: 1)
IPRNAL;

(S3)                                                                (SEQ ID NO: 3)
RNAL; or, (S7)                                                                (SEQ ID NO: 7)
        GTTASSDTAITLIPR.--

Signed and Sealed this
Twenty-fourth Day of March, 2020

Andrei Iancu
*Director of the United States Patent and Trademark Office*